United States Patent
Johnston et al.

(10) Patent No.: US 8,932,372 B2
(45) Date of Patent: *Jan. 13, 2015

(54) INTEGRATED PROCESS FOR PRODUCING ALCOHOLS FROM A MIXED ACID FEED

(75) Inventors: Victor Johnston, Houston, TX (US); Lincoln Sarager, Houston, TX (US); Mark Scates, Houston, TX (US); Ronald David Shaver, Houston, TX (US); G. Paull Torrence, League City, TX (US); R. Jay Warner, Houston, TX (US); Heiko Weiner, Pasadena, TX (US); Trinity Horton, Houston, TX (US); Radmila Jevtic, Pasadena, TX (US); James Zink, League City, TX (US); David Lee, Seabrook, TX (US)

(73) Assignee: Celanese International Corporation, Dallas, TX (US)

( * ) Notice: Subject to any disclaimer, the term of this patent is extended or adjusted under 35 U.S.C. 154(b) by 357 days.

This patent is subject to a terminal disclaimer.

(21) Appl. No.: 13/197,760

(22) Filed: Aug. 3, 2011

(65) Prior Publication Data
US 2012/0036769 A1    Feb. 16, 2012

Related U.S. Application Data

(63) Continuation of application No. 12/889,260, filed on Sep. 23, 2010.

(60) Provisional application No. 61/300,815, filed on Feb. 2, 2010, provisional application No. 61/332,727, filed on May 7, 2010, provisional application No. 61/332,696, filed on May 7, 2010.

(51) Int. Cl.
*C10L 1/182* (2006.01)
*C09K 3/00* (2006.01)
(Continued)

(52) U.S. Cl.
CPC ............... *C07C 29/149* (2013.01); *C07C 29/84* (2013.01); *C10L 1/023* (2013.01); *C10L 1/026* (2013.01); *C10L 1/1824* (2013.01); *C10L 1/18* (2013.01)
USPC .............................. 44/451; 560/265; 252/364

(58) Field of Classification Search
USPC .................... 562/517; 568/902, 885; 252/364; 44/451; 560/265
See application file for complete search history.

(56) References Cited

U.S. PATENT DOCUMENTS

| | | |
|---|---|---|
| 1,939,116 A | 12/1933 | Fuchs |
| 2,105,540 A | 1/1938 | Lazier |

(Continued)

FOREIGN PATENT DOCUMENTS

| | | |
|---|---|---|
| CN | 1230458 | 10/1999 |
| CN | 102091429 | 6/2011 |

(Continued)

OTHER PUBLICATIONS

Jones, J. H., "The Cativa Process for the Manufacture of Acetic Acid", Platinum Metals Review, 44 (3), pp. 94-105 (2000).

(Continued)

*Primary Examiner* — Prem C Singh
*Assistant Examiner* — Chantel Graham

(57) ABSTRACT

Processes for producing alcohols such as ethanol and propanol from a mixed acid feedstock in an integrated process. In one embodiment, the process comprises the step of carbonylating methanol in the presence of a carbonylation catalyst to form a mixed acid feedstock comprising acetic acid and one or more higher acids, preferably comprising propionic acid. The mixed acid feed is hydrogenated in the presence of a hydrogenation catalyst to form a crude alcohol product comprising ethanol and one or more higher alcohols, preferably including propanol.

42 Claims, 7 Drawing Sheets

(51) Int. Cl.
  *C07C 69/14* (2006.01)
  *C07C 29/149* (2006.01)
  *C07C 29/84* (2006.01)
  *C10L 1/02* (2006.01)
  *C10L 1/18* (2006.01)

(56) References Cited

U.S. PATENT DOCUMENTS

| | | | |
|---|---|---|---|
| 2,108,133 A | 2/1938 | McCall | |
| 2,192,137 A | 2/1940 | Kvalnes | |
| 2,549,416 A | 4/1951 | Brooks | |
| 2,607,807 A * | 8/1952 | Ford | 568/885 |
| 2,649,407 A | 8/1953 | Harrison et al. | |
| 2,702,783 A | 2/1955 | Harrison et al. | |
| 2,744,939 A | 5/1956 | Kennel | |
| 2,801,209 A | 7/1957 | Muller et al. | |
| 2,882,244 A | 4/1959 | Milton | |
| 3,130,007 A | 4/1964 | Breck | |
| 3,408,267 A | 10/1968 | Miller et al. | |
| 3,445,345 A | 5/1969 | Katzen et al. | |
| 3,478,112 A | 11/1969 | Karl et al. | |
| 3,702,886 A | 11/1972 | Argauer et al. | |
| 3,729,429 A | 4/1973 | Robson | |
| 3,769,329 A | 10/1973 | Paulik | |
| 3,772,380 A | 11/1973 | Paulik | |
| 3,847,756 A | 11/1974 | Statman et al. | |
| 3,953,524 A | 4/1976 | Steiner | |
| 3,990,952 A | 11/1976 | Katzen et al. | |
| 4,007,130 A | 2/1977 | Leach | |
| 4,052,467 A | 10/1977 | Mills et al. | |
| 4,065,512 A | 12/1977 | Cares | |
| 4,102,922 A | 7/1978 | Price | |
| 4,270,015 A | 5/1981 | Knifton et al. | |
| 4,275,228 A | 6/1981 | Gruffaz et al. | |
| 4,306,942 A | 12/1981 | Brush et al. | |
| 4,317,918 A | 3/1982 | Takano et al. | |
| 4,319,058 A | 3/1982 | Kulprathipanja et al. | |
| 4,328,373 A | 5/1982 | Strojny | |
| 4,337,351 A | 6/1982 | Larkins | |
| 4,379,028 A | 4/1983 | Berg et al. | |
| 4,395,576 A | 7/1983 | Kwantes et al. | |
| 4,398,039 A | 8/1983 | Pesa et al. | |
| 4,399,305 A | 8/1983 | Schreck et al. | |
| 4,421,939 A | 12/1983 | Kiff et al. | |
| 4,422,903 A | 12/1983 | Messick et al. | |
| 4,426,541 A | 1/1984 | King | |
| 4,443,639 A | 4/1984 | Pesa et al. | |
| 4,451,677 A | 5/1984 | Bradley et al. | |
| 4,454,358 A | 6/1984 | Kummer et al. | |
| 4,465,854 A | 8/1984 | Pond et al. | |
| 4,465,875 A | 8/1984 | Greenbank et al. | |
| 4,471,136 A | 9/1984 | Larkins et al. | |
| 4,480,115 A | 10/1984 | McGinnis | |
| 4,492,808 A | 1/1985 | Hagen et al. | |
| 4,497,967 A | 2/1985 | Wan | |
| 4,514,515 A | 4/1985 | Travers et al. | |
| 4,517,391 A | 5/1985 | Schuster et al. | |
| 4,520,213 A | 5/1985 | Victor | |
| 4,521,630 A | 6/1985 | Wattimena et al. | |
| 4,527,995 A | 7/1985 | Itow | |
| 4,541,897 A | 9/1985 | Sommer et al. | |
| 4,550,185 A | 10/1985 | Mabry et al. | |
| 4,559,109 A | 12/1985 | Lee et al. | |
| 4,569,726 A | 2/1986 | Berg et al. | |
| 4,571,391 A | 2/1986 | Riley et al. | |
| 4,581,473 A | 4/1986 | Polichnowski et al. | |
| 4,592,806 A | 6/1986 | Ilgner et al. | |
| 4,613,700 A | 9/1986 | Maki et al. | |
| 4,626,321 A | 12/1986 | Grethlein et al. | |
| 4,626,604 A | 12/1986 | Hiles et al. | |
| 4,678,543 A | 7/1987 | Houben et al. | |
| 4,692,218 A | 9/1987 | Houben et al. | |
| 4,696,596 A | 9/1987 | Russell et al. | |
| 4,760,171 A | 7/1988 | Isogai et al. | |
| 4,762,817 A | 8/1988 | Logsdon et al. | |
| 4,777,303 A | 10/1988 | Kitson et al. | |
| 4,804,791 A | 2/1989 | Kitson et al. | |
| 4,826,795 A | 5/1989 | Kitson et al. | |
| 4,842,693 A | 6/1989 | Wheldon | |
| 4,876,402 A | 10/1989 | Logsdon et al. | |
| 4,886,905 A | 12/1989 | Larkins et al. | |
| 4,961,826 A | 10/1990 | Grethlein et al. | |
| 4,985,572 A | 1/1991 | Kitson et al. | |
| 4,990,655 A | 2/1991 | Kitson et al. | |
| 4,994,608 A | 2/1991 | Torrence | |
| 5,001,259 A | 3/1991 | Smith | |
| 5,004,845 A | 4/1991 | Bradley et al. | |
| 5,008,235 A | 4/1991 | Wegman et al. | |
| 5,026,908 A | 6/1991 | Smith | |
| 5,035,776 A | 7/1991 | Knapp | |
| 5,061,671 A | 10/1991 | Kitson et al. | |
| 5,070,016 A | 12/1991 | Hallberg et al. | |
| 5,093,534 A | 3/1992 | Ludwig et al. | |
| 5,124,004 A | 6/1992 | Grethlein et al. | |
| 5,137,861 A | 8/1992 | Shih et al. | |
| 5,144,068 A | 9/1992 | Smith | |
| 5,149,680 A | 9/1992 | Kitson et al. | |
| 5,155,084 A | 10/1992 | Horn et al. | |
| 5,185,481 A | 2/1993 | Muto et al. | |
| 5,206,434 A | 4/1993 | Scates et al. | |
| 5,215,902 A | 6/1993 | Tedder | |
| 5,233,099 A | 8/1993 | Tabata et al. | |
| 5,237,108 A | 8/1993 | Marraccini et al. | |
| 5,241,106 A | 8/1993 | Inoue et al. | |
| 5,243,095 A | 9/1993 | Roberts et al. | |
| 5,250,271 A | 10/1993 | Horizoe et al. | |
| 5,284,983 A | 2/1994 | Muto et al. | |
| 5,306,845 A | 4/1994 | Yokohama et al. | |
| 5,334,769 A | 8/1994 | Ferrero et al. | |
| 5,348,625 A | 9/1994 | Berg | |
| 5,350,504 A | 9/1994 | Dessau | |
| 5,399,752 A | 3/1995 | Okrasinski et al. | |
| 5,415,741 A | 5/1995 | Berg | |
| 5,426,246 A | 6/1995 | Nagahara et al. | |
| 5,437,770 A | 8/1995 | Berg | |
| 5,445,716 A | 8/1995 | Berg | |
| 5,449,440 A | 9/1995 | Rescalli et al. | |
| 5,475,144 A | 12/1995 | Watson et al. | |
| 5,476,827 A | 12/1995 | Ferrero et al. | |
| 5,480,665 A | 1/1996 | Smith | |
| 5,488,185 A | 1/1996 | Ramachandran et al. | |
| 5,502,248 A | 3/1996 | Funk et al. | |
| 5,527,969 A | 6/1996 | Kaufhold et al. | |
| 5,565,068 A | 10/1996 | Parker et al. | |
| RE35,377 E | 11/1996 | Steinberg et al. | |
| 5,585,523 A | 12/1996 | Weiguny et al. | |
| 5,599,976 A | 2/1997 | Scates | |
| 5,663,430 A | 9/1997 | Morris et al. | |
| 5,672,743 A | 9/1997 | Garland | |
| 5,720,784 A | 2/1998 | Killick | |
| 5,762,765 A | 6/1998 | Berg | |
| 5,767,307 A | 6/1998 | Ramprasad et al. | |
| 5,770,770 A | 6/1998 | Kim et al. | |
| 5,800,681 A | 9/1998 | Berg | |
| 5,821,111 A | 10/1998 | Grady | |
| 5,849,657 A | 12/1998 | Rotgerink et al. | |
| 5,858,031 A | 1/1999 | Perlman | |
| 5,861,530 A | 1/1999 | Atkins et al. | |
| 5,877,348 A | 3/1999 | Ditzel | |
| 5,917,089 A | 6/1999 | Howard | |
| 5,945,570 A | 8/1999 | Arhancet et al. | |
| 5,955,397 A | 9/1999 | Didillon et al. | |
| 5,973,193 A | 10/1999 | Crane et al. | |
| 5,993,610 A | 11/1999 | Berg | |
| 6,040,474 A | 3/2000 | Jobson et al. | |
| 6,049,008 A | 4/2000 | Roberts et al. | |
| 6,093,845 A | 7/2000 | Van Acker et al. | |
| 6,114,571 A | 9/2000 | Abel et al. | |
| 6,121,498 A | 9/2000 | Tustin et al. | |
| 6,140,535 A | 10/2000 | Williams | |
| 6,143,930 A | 11/2000 | Singh | |
| 6,232,352 B1 | 5/2001 | Vidalin et al. | |
| 6,232,504 B1 | 5/2001 | Barteau et al. | |
| 6,294,703 B1 | 9/2001 | Hara et al. | |

(56) References Cited

U.S. PATENT DOCUMENTS

| | | |
|---|---|---|
| 6,326,515 B1 | 12/2001 | Clode et al. |
| 6,375,807 B1 | 4/2002 | Nieuwoudt et al. |
| 6,458,996 B1 | 10/2002 | Muskett |
| 6,462,231 B1 | 10/2002 | Yanagawa et al. |
| 6,472,555 B2 | 10/2002 | Choudary et al. |
| 6,486,366 B1 | 11/2002 | Ostgard et al. |
| 6,495,730 B1 | 12/2002 | Konishi et al. |
| 6,509,180 B1 | 1/2003 | Verser et al. |
| 6,509,290 B1 | 1/2003 | Vaughn et al. |
| 6,559,333 B1 | 5/2003 | Brunelle et al. |
| 6,603,038 B1 | 8/2003 | Hagemeyer et al. |
| 6,627,770 B1 | 9/2003 | Cheung |
| 6,632,330 B1 | 10/2003 | Colley et al. |
| 6,657,078 B2 | 12/2003 | Scates |
| 6,685,754 B2 | 2/2004 | Kindig |
| 6,693,213 B1 | 2/2004 | Kolena et al. |
| 6,696,596 B1 | 2/2004 | Herzog et al. |
| 6,723,886 B2 | 4/2004 | Allison et al. |
| 6,727,380 B2 | 4/2004 | Ellis et al. |
| 6,765,110 B2 | 7/2004 | Warner et al. |
| 6,768,021 B2 | 7/2004 | Horan et al. |
| 6,809,217 B1 | 10/2004 | Colley et al. |
| 6,812,372 B2 | 11/2004 | Janssen et al. |
| 6,852,877 B1 | 2/2005 | Zeyss et al. |
| 6,903,045 B2 | 6/2005 | Zoeller et al. |
| 6,906,228 B2 | 6/2005 | Fischer et al. |
| 6,927,048 B2 | 8/2005 | Verser et al. |
| 7,005,541 B2 | 2/2006 | Cheung |
| 7,074,603 B2 | 7/2006 | Verser et al. |
| 7,084,312 B1 | 8/2006 | Huber et al. |
| 7,115,772 B2 | 10/2006 | Picard |
| 7,199,276 B2 | 4/2007 | Sher |
| 7,208,624 B2 | 4/2007 | Scates |
| 7,297,236 B1 | 11/2007 | Vander Griend et al. |
| 7,351,559 B2 | 4/2008 | Verser et al. |
| 7,375,049 B2 | 5/2008 | Hayes et al. |
| 7,399,892 B2 | 7/2008 | Rix et al. |
| 7,425,657 B1 | 9/2008 | Elliott et al. |
| 7,507,562 B2 | 3/2009 | Verser et al. |
| 7,538,060 B2 | 5/2009 | Barnicki et al. |
| 7,553,397 B1 | 6/2009 | Colley et al. |
| 7,572,353 B1 | 8/2009 | Vander et al. |
| 7,601,865 B2 | 10/2009 | Verser et al. |
| 7,608,744 B1 | 10/2009 | Johnston |
| 7,678,940 B2 | 3/2010 | Miura et al. |
| 7,682,812 B2 | 3/2010 | Verser et al. |
| 7,700,814 B2 | 4/2010 | Garton et al. |
| 7,718,039 B2 | 5/2010 | Dirkzwager et al. |
| 7,732,173 B2 | 6/2010 | Mairal et al. |
| 7,744,727 B2 | 6/2010 | Blum et al. |
| 7,816,565 B2 | 10/2010 | Johnston et al. |
| 7,820,852 B2 | 10/2010 | Johnston et al. |
| 7,834,223 B2 | 11/2010 | Atkins |
| 7,842,844 B2 | 11/2010 | Atkins |
| 7,855,303 B2 | 12/2010 | Johnston et al. |
| 7,863,489 B2 | 1/2011 | Johnston et al. |
| 7,884,253 B2 | 2/2011 | Stites |
| 7,888,082 B2 | 2/2011 | Verser et al. |
| 7,947,746 B2 | 5/2011 | Daniel et al. |
| 8,071,821 B2 | 12/2011 | Johnston et al. |
| 8,541,633 B2 | 9/2013 | Horton et al. |
| 2003/0004057 A1 | 1/2003 | Yamaguchi et al. |
| 2003/0013908 A1 | 1/2003 | Horan et al. |
| 2003/0077771 A1 | 4/2003 | Verser et al. |
| 2003/0104587 A1 | 6/2003 | Verser et al. |
| 2003/0114719 A1 | 6/2003 | Fischer et al. |
| 2003/0191020 A1 | 10/2003 | Bharadwaj et al. |
| 2004/0195084 A1 | 10/2004 | Hetherington et al. |
| 2005/0028435 A1 | 2/2005 | Pace et al. |
| 2005/0176996 A1 | 8/2005 | Law et al. |
| 2006/0019360 A1 | 1/2006 | Verser et al. |
| 2006/0102520 A1 | 5/2006 | Lapinski et al. |
| 2006/0127999 A1 | 6/2006 | Verser et al. |
| 2007/0031954 A1 | 2/2007 | Mairal et al. |
| 2007/0106246 A1 | 5/2007 | Modesitt |
| 2007/0238906 A1 | 10/2007 | Brown et al. |
| 2007/0270511 A1 | 11/2007 | Melnichuk et al. |
| 2008/0135396 A1 | 6/2008 | Blum |
| 2008/0193989 A1 | 8/2008 | Verser et al. |
| 2008/0207953 A1 | 8/2008 | Houssin et al. |
| 2009/0005588 A1 | 1/2009 | Hassan et al. |
| 2009/0014313 A1 | 1/2009 | Lee et al. |
| 2009/0023192 A1 | 1/2009 | Verser et al. |
| 2009/0069609 A1 | 3/2009 | Kharas et al. |
| 2009/0081749 A1 | 3/2009 | Verser et al. |
| 2009/0166172 A1 | 7/2009 | Casey et al. |
| 2009/0209786 A1* | 8/2009 | Scates et al. .................. 562/517 |
| 2009/0221725 A1 | 9/2009 | Chornet et al. |
| 2009/0259086 A1 | 10/2009 | Bailey |
| 2009/0274480 A1 | 11/2009 | Zona |
| 2009/0281354 A1 | 11/2009 | Mariansky et al. |
| 2009/0299092 A1 | 12/2009 | Beavis et al. |
| 2009/0318573 A1 | 12/2009 | Stites |
| 2009/0326080 A1 | 12/2009 | Chornet et al. |
| 2010/0016454 A1 | 1/2010 | Gracey et al. |
| 2010/0029980 A1 | 2/2010 | Johnston et al. |
| 2010/0029993 A1 | 2/2010 | Johnston et al. |
| 2010/0029995 A1 | 2/2010 | Johnston |
| 2010/0029996 A1 | 2/2010 | Danjo et al. |
| 2010/0030001 A1 | 2/2010 | Chen |
| 2010/0030002 A1 | 2/2010 | Johnston |
| 2010/0069514 A1 | 3/2010 | Gracey et al. |
| 2010/0069515 A1 | 3/2010 | Tirtowidjojo et al. |
| 2010/0113843 A1 | 5/2010 | Lee et al. |
| 2010/0121114 A1 | 5/2010 | Johnston et al. |
| 2010/0125148 A1 | 5/2010 | Johnston et al. |
| 2010/0137630 A1 | 6/2010 | Garton et al. |
| 2010/0168467 A1 | 7/2010 | Johnston et al. |
| 2010/0168493 A1 | 7/2010 | Le Peltier et al. |
| 2010/0185021 A1 | 7/2010 | Ross et al. |
| 2010/0196789 A1 | 8/2010 | Fisher et al. |
| 2010/0197485 A1 | 8/2010 | Johnston |
| 2010/0197959 A1 | 8/2010 | Johnston et al. |
| 2010/0197985 A1 | 8/2010 | Johnston et al. |
| 2010/0249479 A1 | 9/2010 | Berg-Slot et al. |
| 2011/0004033 A1 | 1/2011 | Johnston et al. |
| 2011/0004034 A1* | 1/2011 | Daniel et al. .................. 568/902 |
| 2011/0046421 A1 | 2/2011 | Daniel et al. |
| 2011/0071312 A1 | 3/2011 | Johnston et al. |
| 2011/0082322 A1 | 4/2011 | Jevtic et al. |
| 2011/0098513 A1 | 4/2011 | Weiner |
| 2011/0190547 A1 | 8/2011 | Jevtic et al. |
| 2011/0190548 A1 | 8/2011 | Jevtic et al. |
| 2011/0237837 A1 | 9/2011 | Al-Rabiah et al. |
| 2011/0275865 A1 | 11/2011 | Warner et al. |

FOREIGN PATENT DOCUMENTS

| | | |
|---|---|---|
| CN | 102228831 | 11/2011 |
| CN | 102229520 | 11/2011 |
| DE | 2723611 | 11/1978 |
| DE | 3221077 | 12/1983 |
| EP | 0056488 | 7/1982 |
| EP | 0104197 | 4/1984 |
| EP | 0137749 | 4/1985 |
| EP | 0167300 | 1/1986 |
| EP | 0175558 | 3/1986 |
| EP | 0192587 | 8/1986 |
| EP | 0198682 | 10/1986 |
| EP | 0253540 | 1/1988 |
| EP | 0285420 | 10/1988 |
| EP | 0285786 | 10/1988 |
| EP | 0400904 | 5/1990 |
| EP | 0372847 | 6/1990 |
| EP | 0408528 | 7/1990 |
| EP | 0456647 | 11/1991 |
| EP | 0539274 | 4/1993 |
| EP | 0557786 | 9/1993 |
| EP | 0849248 | 6/1998 |
| EP | 0953560 | 11/1999 |
| EP | 0990638 | 4/2000 |
| EP | 0992482 | 4/2000 |
| EP | 0992484 | 4/2000 |
| EP | 1262234 | 12/2002 |

(56) References Cited

FOREIGN PATENT DOCUMENTS

| | | |
|---|---|---|
| EP | 1277826 | 1/2003 |
| EP | 2060553 | 5/2009 |
| EP | 2060555 | 5/2009 |
| EP | 2072487 | 6/2009 |
| EP | 2072488 | 6/2009 |
| EP | 2072489 | 6/2009 |
| EP | 2072492 | 6/2009 |
| EP | 2186787 | 5/2010 |
| GB | 745946 | 3/1956 |
| GB | 1168785 | 10/1969 |
| GB | 1276326 | 6/1972 |
| GB | 1559540 | 1/1980 |
| GB | 2136704 | 9/1984 |
| JP | 4-193304 | 7/1992 |
| JP | 6-116182 | 4/1994 |
| JP | 10-306047 | 11/1998 |
| JP | 11-147845 | 6/1999 |
| JP | 2001-046874 | 2/2001 |
| JP | 2001-157841 | 6/2001 |
| JP | 2010-159212 | 7/2010 |
| WO | WO 83/03409 | 10/1983 |
| WO | WO 03/040037 | 5/2003 |
| WO | WO 03/106396 | 12/2003 |
| WO | 2004026805 | 4/2004 |
| WO | WO 2007/003897 | 1/2007 |
| WO | 2007071902 | 6/2007 |
| WO | WO 2007/145490 | 12/2007 |
| WO | WO 2008/098254 | 8/2008 |
| WO | WO 2008/135192 | 11/2008 |
| WO | WO 2009/009322 | 1/2009 |
| WO | WO 2009/009323 | 1/2009 |
| WO | WO 2009/048335 | 4/2009 |
| WO | WO 2009/063176 | 5/2009 |
| WO | WO 2009/103948 | 8/2009 |
| WO | WO 2009/105860 | 9/2009 |
| WO | WO 2010/014145 | 2/2010 |
| WO | WO 2010/014146 | 2/2010 |
| WO | WO 2010/014148 | 2/2010 |
| WO | WO 2010/014151 | 2/2010 |
| WO | WO 2010/014152 | 2/2010 |
| WO | WO 2010/014153 | 2/2010 |
| WO | WO 2010/055285 | 5/2010 |
| WO | WO 2010/056299 | 5/2010 |
| WO | WO 2011/053365 | 5/2011 |
| WO | WO 2011/097227 | 8/2011 |

OTHER PUBLICATIONS

Waterland et al., Safety and Performance Assessment of Ethanol/Diesel Blends (E-Diesel), NREL/SR-540-34817, at p. 1-1 (Sep. 2003).
International Fuel Quality Center Hart Downstream Energy Services: "Setting a Quality Standard for Fuel-Ethanol-Standard 18/2004 Report", Jan. 1, 2004, pp. 1-56.
International Preliminary Report on Patentability mailed Dec. 13, 2012 in corresponding International Application No. PCT/US2011/046508.
International Written Opinion mailed Sep. 26, 2012 in corresponding International Application No. PCT/US2011/046508.
International Search Report and Written Opinion mailed Feb. 2, 2012 in corresponding International Application No. PCT/US2011/046508.
Zhang et al., Hydrogenation of Ethyl Acetate to Ethanol over Ni-Based Catalysts Obtained from Ni/Al Hydrotalcite-Like Compounds. Molecules 2010, 15, 5139-5152, 2010.
Zheng, et al. (2007). Preparation and catalytic properties of a bimetallic Sn-Pt complex in the supercages of NaY zeolite by use of surface organometallic chemistry, Applied Organometallic Chemistry, 21(10), 836-840.
ZeaChem, Inc., Technology Overview, Lakewood, Colorado www.zeachem.com, 2008.
Santori et al.(2000). Hydrogenation of carbonylic compounds on Pt/SiO2 catalysts modified with SnBu4, Studies in Surface Science and Catalysis, 130, 2063-2068.
Rachmady, Acetic Acid Reduction by H2 on Bimetallic Pt—Fe Catalysts, Journal of Catalysis 209, 87-98 (Apr. 1, 2002), Elsevier Science (USA).
Pestman et al., The formation of ketones and aldehydes from carboxylic acids, structure-activity relationship for two competitive reactions, Journal of Molecular Catalysis A: Chemical 103 Jun. 14, 1995, 175-180.
Pestman et al., Reactions of Carboxylic Acids on Oxides, Journal of Catalysis 168:255-264 (1997).
Pestman et al., Identification of the Active Sites in the Selective Hydrogenation of Acetic Acid to Acetaldehyde on Iron Oxide Catalysts, Journal of Catalysis 174:142-152 (1998).
Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.
Ordóñez et al., The role of metal and support sites on the hydrogenation of acetic acid on Ru-based catalysts, 21st NAM San Francisco, CA, Jun. 10, 2009.
Hilmen, Separation of Azeotropic Mixtures: Tools for Analysis and Studies on Batch Distillation Operation (Nov. 2000) p. 17-20.
Gursahani et al., Reaction kinetics measurements and analysis of reaction pathways for conversions of acetic acid, ethanol, and ethyl acetate over silica-supported Pt, Applied Catalysis A: General 222 (2001) 369-392.
Amit M. Goda et al., DFT modeling of selective reduction of acetic acid to acetaldehyde on Pt-based bimetallic catalysts, 20th NAM, Houston, TX, Jun. 17-22, 2007 available online at <http://www.nacatsoc.org/20nam/abstracts/O-S9-18.pdf>.
Acala, et al., (2005). Experimental and DFT studies of the conversion of ethanol and acetic acid on PtSn-based catalysts, Journal of Physical Chemistry, 109(6), 2074-2085.
Brunauer Emmett and Teller, J. Am. Chem. Soc. 60, 309 (1938).
Invitation to Pay Additional Fees and Partial Search Report for PCT/US2011/023331 mailed May 4, 2011.
International Search Report and Written Opinion for PCT/US2010/054136 mailed May 25, 2011.
International Search Report and Written Opinion for PCT/US2011/023338 mailed Sep. 6, 2011.
International Search Report for PCT/US2011/023269 mailed Aug. 25, 2010.
International Search Report for PCT/US2011/046508 dated Mar. 29, 2012.
International Search and Written Opinion for PCT/US2011/046508 mailed Feb. 2, 2012.
International Search Report for PCT/US2011/046500 dated Mar. 29, 2012.
Invitation to Pay Fees for PCT/US2011/046493 dated Feb. 6, 2012.
International Search Report and Written Opinion for PCT/US2011/023322 mailed Sep. 6, 2011.
International Search Report and Written Opinion for PCT/US2009/004197 mailed Mar. 24, 2010 (14 pages).
International Search Report and Written Opinion for PCT/US2009/004195 mailed Mar. 26, 2010 (12 pages).
International Search Report and Written Opinion for PCT/US2010/022947 mailed Jun. 7, 2010.
Office Action for U.S. Appl. No. 13/273,054 dated Jun. 20, 2012.
Yamada, et al., Journal of Molecular Catalysis: Chemical, 2011, 346, pp. 79-86.
International Preliminary Report on Patentability for PCT/US2011/023322 mailed Jun. 27, 2012.
Non-final Office Action for U.S. Appl. No. 13/197,720 mailed Oct. 1, 2013.
Ethanol Guidelines (HODAC) 2009.
Office Action for U.S. Appl. No. 13/197,720 dated Jan. 22, 2014.

* cited by examiner

US 8,932,372 B2

INTEGRATED PROCESS FOR PRODUCING ALCOHOLS FROM A MIXED ACID FEED

CROSS REFERENCE TO RELATED APPLICATIONS

This is a continuation-in-part of U.S. application Ser. No. 12/889,260, filed Sep. 23, 2010, which claims priority to U.S. Provisional Application No. 61/300,815, filed Feb. 2, 2010, U.S. Provisional Application No. 61/332,727, filed May 7, 2010, and U.S. Provisional Application No. 61/332,696, filed May 7, 2010, the entireties of which are incorporated herein by reference.

FIELD OF THE INVENTION

The present invention relates generally to processes for producing alcohol compositions and, in particular, to processes for producing ethanol compositions via the synthesis of a mixed acid feed comprising acetic acid and a higher acid, and hydrogenating the mixed acid feed to form ethanol and a higher alcohol.

BACKGROUND OF THE INVENTION

Ethanol for industrial use is conventionally produced from petrochemical feed stocks, such as oil, natural gas, or coal, from feed stock intermediates, such as syngas, or from starchy materials or cellulose materials, such as corn or sugar cane. Conventional methods for producing ethanol from petrochemical feed stocks, as well as from cellulose materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulose material, are converted to ethanol by fermentation. However, fermentation is typically used for consumer production of ethanol, which is suitable for fuels or human consumption. In addition, fermentation of starchy or cellulose materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. During the reduction of alkanoic acid, e.g., acetic acid, other compounds are formed with ethanol or are formed in side reactions. These impurities limit the production and recovery of ethanol from such reaction mixtures. For example, during hydrogenation, esters are produced that together with ethanol and/or water form azeotropes, which are difficult to separate. In addition when conversion is incomplete, unreacted acid remains in the crude ethanol product, which must be removed to recover ethanol.

Alkanoic acids, such as acetic acid, used in the production of ethanol are commonly synthesized by the catalyzed carbonylation of methanol with carbon monoxide as taught in U.S. Pat. No. 3,769,329, incorporated herein by reference in its entirety. The carbonylation catalyst contains rhodium, either dissolved or otherwise dispersed in a liquid reaction medium or supported on an inert solid, along with a halogen-containing catalyst promoter as exemplified by methyl iodide. The rhodium can be introduced into the reaction system in any of many forms. Likewise, because the nature of the halide promoter is not generally critical, a large number of suitable promoters, most of which are organic iodides, may be used. Most typically and usefully, the reaction is conducted by continuously bubbling carbon monoxide gas through a liquid reaction medium in which the catalyst is dissolved.

Carbonylation processes in the presence of iridium catalysts are also known and are described, for example, in U.S. Pat. No. 3,772,380 and in U.S. Pat. No. 5,672,743, the entireties of which are incorporated herein by reference. UK patent GB 1276326 describes the preparation of monocarboxylic acids and their esters by carbonylation of alcohols, halides, ethers, esters or 1,2 epoxy aliphatic compounds in the presence of rhodium or iridium catalysts, halogen promoters and water or an alcohol, ether or ester.

Both Iridium and Rhodium based carbonylation catalysts suffer in that may tend to form impurities such as propionic acid, typically necessitating multiple columns to form a suitable acetic acid product having desired purity. Significant capital and operational costs are also incurred by the necessity of operating a large distillation column (commonly referred to as a "Heavies" or "Heavy Ends" column) to remove low levels of high boiling point impurities, with propionic acid being the major component.

The need therefore exists for new processes for mitigating impurities, such as propionic acid, that are commonly formed in the synthesis of acetic acid. The need also exists for improved processes for synthesizing ethanol from a crude product obtained by reducing alkanoic acids, such as acetic acid, and/or other carbonyl group-containing compounds.

SUMMARY OF THE INVENTION

In a first embodiment, the present invention is to a process for producing an alcohol composition comprising the step of carbonylating methanol in a carbonylation reactor to form a mixed acid feed comprising acetic acid and at least 0.01 wt. % heavier acid. The process further comprises the steps of hydrogenating the mixed acid feed comprising acetic acid in the presence of a catalyst to form a crude alcohol product comprising ethanol and a higher alcohol; and separating the crude alcohol product in one or more separation units to form an alcohol composition and one or more derivative streams.

In one embodiment, the separating step separates the crude alcohol product to form a mixed alcohol composition and one or more derivative streams. Preferably, the mixed alcohol composition comprises ethanol in an amount greater than 60 wt. % and the higher alcohol in an amount from 0.01 wt. % to 40 wt %, based on the total weight of the mixed alcohol composition.

BRIEF DESCRIPTION OF DRAWINGS

The invention is described in detail below with reference to the appended drawings, wherein like numerals designate similar parts.

DETAILED DESCRIPTION OF THE INVENTION

Introduction

Figure 1A:
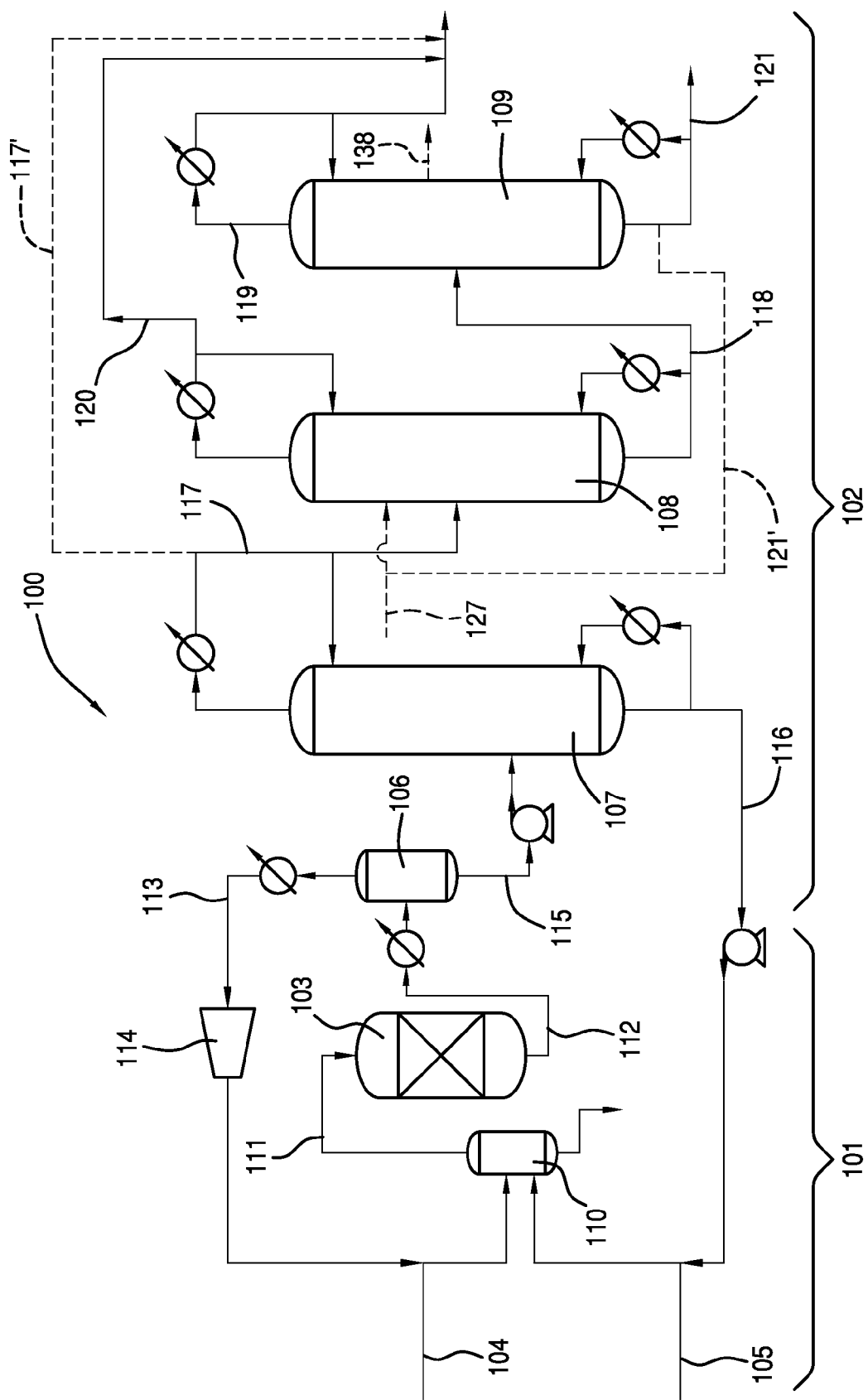
FIG. 1A is a schematic diagram of a hydrogenation system in accordance with one embodiment of the present invention.

The present invention relates to processes for producing alcohols such as ethanol and propanol from a mixed acid feedstock. It has now been discovered that catalysts suitable for the hydrogenation of acetic acid to form ethanol also may tolerate higher acids, such as propionic acid. Moreover, the catalysts catalyze the hydrogenation of the one or more higher acids, such as propionic acid, to the corresponding higher alcohols, such as propanol, which may be desirable to form a denatured ethanol composition comprising primarily ethanol and a minor amount of higher alcohol as denaturant. In this context, the term "higher" means $C_{3+}$ compounds. The resulting crude mixed alcohol product may be separated to form a product ethanol stream and a product higher alcohol stream (preferably a product propanol stream), or may be purified as a mixed alcohol product and made salable, for example, as a mixed alcohol composition, optionally a denatured ethanol composition, in which the denaturant comprises one or more higher alcohols, preferably propanol.

It has now been discovered that the ability of the catalytic hydrogenation process to receive one or more higher acids, such as propionic acid, in addition to acetic acid, lends itself well to being integrated with a process for forming acetic acid that also forms one or more higher acids, e.g., propionic acid. In particular, by incorporating the hydrogenation process with the acid synthesis process, the acid separation scheme may be significantly simplified to form a crude acetic acid feed comprising acetic acid and propionic acid suitable for hydrogenation in the catalytic hydrogenation process of the invention.

Thus, in one embodiment, the invention relates to an integrated process for forming acetic acid in a carbonylation process and hydrogenating the acetic acid to form ethanol. In one embodiment, for example, the invention is to a process for producing an alcohol composition, the process comprising: (a) carbonylating methanol in a carbonylation reactor to form a mixed acid feed comprising acetic acid and at least 0.01 wt. % heavier acid, e.g., propionic acid; (b) hydrogenating the mixed acid feed comprising acetic acid in the presence of a catalyst to form a crude alcohol product comprising ethanol and a higher alcohol, e.g., propanol; and (c) separating the crude alcohol product in one or more separation units to form an alcohol composition and one or more derivative streams.

In a preferred aspect, the carbonylating step forms a crude acetic acid product, and the process further comprises the steps of separating the crude acetic acid product in a flash unit to form a flashed stream and a catalyst recycle stream; and separating, in no more than one separation column, the flashed stream into a distillate comprising an alkyl halide and an alkyl acetate, and a residue comprising the mixed acid feed. By employing no more than one separation column, typically a light ends column, the present invention advantageously results in lower overall operating costs in that no drying column or heavy ends column is required.

Thus, in one embodiment, the invention is to a process comprising the steps of hydrogenating acetic acid and one or more higher acids derived from an integrated carbonylation system in the presence of a catalyst to form a crude alcohol product comprising ethanol and one or more higher alcohols, preferably propanol. As used herein, unless otherwise specified, the term "propanol" refers to n-propanol and isopropanol in combination. Preferably, the crude alcohol product comprises ethanol in an amount greater than 60 wt. % and the one or more higher alcohols, preferably propanol, in an amount from 0.1 to 40 wt. %.

In one embodiment, the higher alcohols may act as denaturants that are co-produced with the ethanol. In another embodiment, the higher alcohols are formed as a by-product of the hydrogenation reaction in addition to being formed from the higher acids. In other words, the higher alcohols are formed in situ with the ethanol. The processes of the present invention, in one embodiment, further comprise separating the crude ethanol product into a mixed alcohol composition, optionally a denatured ethanol composition, and one or more derivative streams. The separating may be performed in one or more, e.g., two or more, or three or more, separation units, e.g., distillation columns. The resultant mixed alcohol composition, as formed, is derived from acetic acid and one or more higher acids and comprises from 0.01 wt. % to 40 wt. % higher alcohols, e.g., from 0.01 wt. % to 25 wt. %, from 0.01 wt. % to 20 wt. %, or from 1 wt. % to 15 wt. %, and from 50 wt. % to 99 wt. % ethanol, e.g., from 60 wt. % to 99 wt. % or from 70 wt. % to 95 wt. %, based on the total weight of the mixed alcohol composition. Thus, by forming the higher alcohol in situ along with the ethanol in the hydrogenation step, the inventive processes may produce a mixed alcohol composition, e.g., a denatured ethanol composition, more efficiently and may reduce processing steps. In particular, the processes of the present invention may eliminate the need for separately producing or obtaining a denaturant and subsequently adding the denaturant to ethanol.

The processes of the invention may be beneficial, for example, in forming mixed alcohol compositions that are suitable for blending into various petroleum fuels. As an example, at ethanol contents of 20% and higher, ethanol/Diesel blends ("E-Diesel") cannot be uniformly mixed or blended into one phase without rapid phase separation at temperatures lower than 10° C. Since they cannot be uniformly mixed into one phase and stored for easy use, the components typically must be mixed just prior to use and temperatures below 10° C. should be avoided. One solution to this problem is to blend ethanol with higher alcohols resulting in a mixed alcohol composition that may be blended into diesel fuel oil with reduced or eliminated phase separation issues at normal ambient conditions. See, e.g., U.S. Pat. Nos. 4,527,995 and 5,720,784, and L. R. Waterland et al., *Safety and Performance Assessment of Ethanol/Diesel Blends* (*E-Diesel*), NREL/SR-540-34817, at p. 1-1 (September 2003), the entireties of which are incorporated herein by reference.

Thus, in one embodiment, the invention is a process for forming a mixed alcohol composition for diesel fuel use comprising the steps of hydrogenating acetic acid and one or more higher acids derived from an integrated carbonylation system in the presence of a catalyst to form a crude alcohol product comprising ethanol and one or more higher alcohols, preferably propanol, although for improved blending $C_{4+}$ acids in the feed and $C_{4+}$ alcohols in the crude alcohol product may be desired. The crude alcohol product is separated into a mixed alcohol composition comprising ethanol and the higher alcohol, and one or more derivative streams. The mixed alcohol composition may then be blended with a minor amount of diesel fuel denaturant, e.g., diesel fuel oil, to form a denatured mixed alcohol composition for diesel fuel use.

The denatured mixed alcohol composition for diesel fuel use preferably comprises from 0.5 to 4 wt. % diesel fuel denaturant, at least 15 wt. % ethanol (e.g., 75-98 wt. % ethanol or 90-98 wt. % ethanol), and at least 0.01 wt. % heavier alcohol (e.g., propanol), e.g., at least 0.04 wt. %, at least 0.5 wt. %, at least 1 wt. %, at least 2 wt. % or at least 5 wt. % heavier alcohol. The invention also relates to processes for blending such denatured mixed alcohol compositions with diesel fuel to form an E-Diesel fuel composition, preferably comprising from 10 to 15 wt % ethanol.

Alternatively, the mixed alcohol composition may be blended with a minor amount of a gasoline fuel denaturant, e.g., natural gasoline, gasoline blendstocks or unleaded gasoline, as defined in ASTM D4806-11, the entirety of which is incorporated herein by reference, to form a denatured mixed alcohol composition. The denatured mixed alcohol composition for gasoline fuel use preferably comprises from 1.5 to 3.0 wt. % gasoline fuel denaturant, at least 92.1 wt. % ethanol (as determined by ASTM D5501, the entirety of which is incorporated herein by reference), and at least 0.01 wt. % heavier alcohol (e.g., propanol), e.g., at least 0.04 wt. %, at least 0.5 wt. %, at least 1 wt. %, at least 2 wt. % or at least 5 wt. % heavier alcohol. The denatured mixed alcohol composition preferably comprises no more than 1.0 wt. % water as determined by ASTM E203. The invention also relates to processes for blending such denatured mixed alcohol compositions with a gasoline fuel to form an ethanol/gasoline composition, optionally an E10, E15, or E85 fuel composition, optionally comprising from 5 to 40 wt. % ethanol, e.g., from 10 to 15 wt % ethanol, about 10 wt. % ethanol, or about 15 wt. % ethanol, or about 85 wt. % ethanol, the remainder consisting essentially of gasoline.

Acetic Acid and Higher Acid Synthesis

Processes for forming acetic acid and one or more higher acids, in particular propionic acid, are well known and are described in the literature. The raw materials, acetic acid, the higher acid and hydrogen, used in connection with the process of this invention may be derived from any suitable source including natural gas, petroleum, coal, biomass, and so forth. The acetic acid preferably is produced via methanol carbonylation, although it may also be formed via acetaldehyde oxidation, ethylene oxidation, oxidative fermentation or anaerobic fermentation. The higher acid, in particular propionic acid, may be formed as a byproduct of the carbonylation process, particularly in the Cativa™ process for producing acetic acid, as described in J. Jones et al., *Platinum Metals Review*, Vol. 44, No. 3, pp. 94-104 (July 2000) and U.S. Pat. No. 6,140,535, the entireties of which are incorporated herein by reference, or in the Monsanto process for producing acetic acid, as described for example in U.S. Pat. Nos. 3,769,329 and 4,102,922, the entireties of which are incorporated herein by reference. Additional methanol carbonylation processes suitable for production of acetic acid, and which may be included in the integrated processes of the present invention, are described in U.S. Pat. Nos. 7,208,624, 7,115,772, 7,005,541, 6,657,078, 6,627,770, 6,143,930, 5,144,068, and 4,994,608, the disclosures of which are incorporated herein by reference. The use of cobalt catalysts has been demonstrated to form propionic acid in relatively large amounts and may also be used in the integrated process of the invention. See, e.g., U.S. Pat. No. 3,772,380, incorporated herein by reference in its entirety.

A. Iridium-Catalyzed Process for Forming Mixed Acid Feed

U.S. Pat. No. 6,140,535, incorporated herein in its entirety and portions of which are reproduced herein, describes process steps for reducing propionic acid content in the Iridium-catalyzed carbonylation of methanol. The '535 patent provides a process for the production of an acetic acid process stream comprising less than 400 ppm propionic acid and less than 1500 ppm water which process comprises the steps of (a) feeding methanol and/or a reactive derivative thereof and carbon monoxide to a carbonylation reactor in which there is maintained during the course of the process a liquid reaction composition comprising: (i) an iridium carbonylation catalyst; (ii) methyl iodide co-catalyst; (iii) optionally one or more promoters selected from the group consisting of ruthenium, osmium, rhenium, cadmium, mercury, zinc, gallium, indium and tungsten; (iv) a finite amount of water at a concentration of less than about 8% by weight; (v) methyl acetate; (vi) acetic acid; and (vii) propionic acid by-product and its precursors; (b) withdrawing liquid reaction composition from the carbonylation reactor and introducing at least part of the withdrawn liquid reaction composition, with or without the addition of heat, to a flash zone to form a vapor fraction comprising water, acetic acid product, propionic acid by-product, methyl acetate, methyl iodide and propionic acid precursors, and a liquid fraction comprising involatile iridium catalyst, involatile optional promoter or promoters, acetic acid and water; (c) recycling the liquid fraction from the flash zone to the carbonylation reactor; (d) introducing the vapor fraction from the flash zone into a first distillation zone; (e) removing from the first distillation zone at a point above the introduction point of the flash zone vapor fraction a light ends recycle stream comprising water, methyl acetate, methyl iodide, acetic acid and propionic acid precursors which stream is recycled in whole or in part to the carbonylation reactor, and (f) removing from the first distillation zone at a point below the introduction point of the flash zone vapor fraction, a process stream comprising acetic acid product, propionic acid by-product, and less than 1500 ppm water and, (g) if the process stream removed in step (f) comprises greater than 400 ppm propionic acid introducing, said stream into a second distillation column, removing from a point below the introduction point of the stream from (f) propionic acid by-product and from a point above the introduction point of the stream from (f) an acetic acid process stream containing less than 400 ppm propionic acid and less than 1500 ppm water.

Thus, the process described in the '535 patent includes a step of sending an acetic acid process stream to a second column, also known as a heavy ends column, for removal of excess propionic acid, when the acetic acid process stream comprises more than 400 ppm propionic acid. The process of the present invention beneficially may tolerate or benefit from the inclusion of such propionic acid in the acetic acid process stream in that the acetic acid may be hydrogenated to form ethanol and the propionic acid may be hydrogenated to form propanol, as described below. Thus, the integrated process of the invention advantageously does not require more than one separation column in the carbonylation separation system even where the acetic acid process stream comprises more than 400 wppm propionic acid. The elimination of a heavy ends column, e.g., propionic acid separation unit, result in significant energy savings in the overall integrated production process. It is contemplated, however, that the integrated process of the invention may also be employed with a carbonylation separation system that employs more than one column so long as the mixed acid feed that is fed to the hydrogenation system comprises one or more heavier acids, e.g., in an amount greater than 0.01 wt. %.

The iridium catalyst in the liquid reaction composition may comprise any iridium-containing compound which is soluble in the liquid reaction composition. The iridium catalyst may be added to the liquid reaction composition for the carbonylation reaction in any suitable form which dissolves in the liquid reaction composition or is convertible to a soluble form. Examples of suitable iridium-containing compounds which may be added to the liquid reaction composition include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^-H^+$, $[Ir(CO)_2Br_2]^-H^+$, $[Ir(CO)_2I_4]^-H^+$, $[Ir(CH_3)I_3(CO)_2]^-H^+$, $Ir_4(CO)_{12}$, $IrCl_3.3H_2O$, $IrBr_3.3H_2O$, $Ir_4(CO)_{12}$, iridium metal, $Ir_2O_3$, $IrO_2$, $Ir(acac)(CO)_2$, $Ir(acac)_3$, iridium acetate, $[Ir_3O(OAc)_6(H_2O)_3][OAc]$, and hexachloroiridic acid$[H_2IrCl_6]$, preferably, chloride-free complexes of iridium such as acetates, oxalates and acetoacetates which are soluble in one or more of the carbonylation reaction components such as water, alcohol and/or carboxylic acid. Particularly preferred is green iridium acetate which may be used in an acetic acid or aqueous acetic acid solution. The concentration of iridium is suitably less than 2500 ppm, preferably from 400 to 2000 ppm.

Optionally one or more promoters may be present in the reaction composition. Suitable promoters are preferably selected from the group consisting, of ruthenium, osmium, rhenium, cadmium, mercury, zinc, gallium, indium and tungsten, and are more preferably selected from ruthenium and osmium and most preferably is ruthenium. Preferably, the promoter is present in an effective amount up to the limit of its solubility in the liquid reaction composition aid/or any liquid process streams recycled to the carbonylation reactor from the acetic acid recovery stage. The promoter is suitably present in the liquid reaction composition at a molar ratio of promoter:iridium of (from 0.5 to 15):1.

The promoter may comprise any suitable promoter metal-containing compound which is soluble in the liquid reaction composition. The promoter may be added to the liquid reaction composition for the carbonylation reaction in any suitable form which dissolves in the liquid reaction composition or is convertible to soluble form. Examples of suitable ruthenium-containing compounds which may be used as sources of promoter include ruthenium (III) chloride, ruthenium (III) chloride trihydrate, ruthenium (IV) chloride, ruthenium (III) bromide, ruthenium metal, ruthenium oxides, ruthenium (III) formate, $[Ru(CO)_3I_3]^-H^+$, $[Ru(CO)_2I_2]_n$, $[Ru(CO)_4I_2]$, $[Ru(CO)_3I_2]_2$, tetra(aceto)chlororuthenium(II,III), ruthenium (III) acetate, ruthenium (III) propionate, ruthenium (III) butyrate, ruthenium pentacarbonyl, triruthenium dodecacarbonyl and mixed ruthenium halocarbonyls such as dichlorotricarbonylruthenium (II) dimer, dibromotricarbonylruthenium (II) dimer, and other organoruthenium complexes such as tetrachlorobis(4-cymene)diruthenium(II), tetrachlorobis(benzene)diruthenium((II), dichloro(cycloocta-1,5-diene)ruthenium (II) polymer and tris(acetylacetonate)ruthenium (III).

Examples of suitable osmium-containing compounds which may be used as sources of promoter include osmium (III) chloride hydrate and anhydrous, osmium metal, osmium tetraoxide, triosmiumdodecacarbonyl, $[Os(CO)_4I_2]$, $[Os(CO)_3I_2]_2$, $[Os(CO)_3I_3]^-H^+$, and mixed osmium halocarbonyls such as tricarbonyldichloroosmium (II) dimer and other organoosmium complexes.

Examples of suitable rhenium-containing compounds which may be used as sources of promoter include $Re_2(CO)_{10}$, $Re(CO)_5Cl$, $Re(CO)_5Br$, $Re(CO)_5I$, $ReCl_3.H_2O[Re(CO)_4I]_2$, $[Re(CO)_4I_2]^-H^+$ and $ReCl_5.yH_2O$.

Examples of suitable cadmium-containing compounds which may be used include $Cd(OAc)_2$, $CdI_2$, $CdBr_2$, $CdCl_2$, $Cd(OH)_2$, and cadmium acetylacetonate.

Examples of suitable mercury-containing compounds which may be used as sources of promoter include $Hg(OAc)_2$, $HgI_2$, $HgBr_2$, $HgCl_2$, $Hg_2I_2$, and $Hg_2Cl_2$.

Examples of suitable zinc-containing compounds which may be used as sources of promoter include $Zn(OAc)_2$, $Zn(OH)_2$, $ZnI_2$, $ZnBr_2$, $ZnCl_2$, and zinc acetylacetonate.

Examples of suitable gallium-containing compounds which may be used as sources of promoter include gallium acetylacetonate, gallium acetate, $GaCl_3$, $GaBr_3$, $GaI_3$, $Ga_2Cl_4$ and $Ga(OH)_3$.

Examples of suitable indium-containing compounds which may be used as sources of promoter include indium acetylacetonate, indium acetate, $InCl_3$, $InBr_3$, $InI_3$, $InI$ and $In(OH)_3$.

Examples of suitable tungsten-containing compounds which may be used as sources of promoter include $W(CO)_6$, $WCl_4$, $WCl_6$, $WBr_5$, $WI_2$, or $C_9H_{12}W(CO)_3$.

Preferably, the iridium- and promoter-containing compounds are free of impurities which provide or generate in situ ionic iodides which may inhibit the reaction, for example, alkali or alkaline earth metal or other metal salts.

Ionic contaminants such as, for example, (a) corrosion metals, particularly nickel, iron and chromium and (b) phosphines or nitrogen-containing compounds or ligands which may quaternize in situ should be kept to a minimum in the liquid reaction composition as these may generally have an adverse effect on the reaction by generating $I^-$ in the liquid reaction composition which may have an adverse effect on the reaction rate. Some corrosion metal contaminants such as for example molybdenum have been found to be less susceptible to the generation of $I^-$ Corrosion metals which have an adverse affect on the reaction rate may be minimized by using suitable corrosion resistant materials of construction. Similarly, contaminants such as alkali metal iodides, for example lithium iodide, may be kept to a minimum. Corrosion metal and other ionic impurities may be reduced by the use of a suitable ion exchange resin bed to treat the reaction composition, or preferably a catalyst recycle stream. Such a process is described in U.S. Pat. No. 4,007,130, incorporated herein by reference. Ionic contaminants may be kept below a concentration at which they would generate less than 500 ppm $I^-$, preferably less than 250 ppm $I^-$ in the liquid reaction composition.

Water may be formed in situ in the liquid reaction composition, for example, by the esterification reaction between methanol reactant and acetic acid product. Water may be introduced to the carbonylation reactor together with or separately from other components of the liquid reaction composition. Water may be separated from other components of the reaction composition withdrawn from the carbonylation reactor and may be recycled in controlled amounts to maintain the required concentration of the water in the liquid reaction composition. Suitably, the concentration of water in the liquid reaction composition is in the range from 0.5 to 8% by weight.

In a further embodiment of the present invention, liquid reaction composition may be withdrawn from the carbonylation reactor and introduced, with or without the addition of heat to a preliminary flash zone. In this preliminary flash zone, a preliminary flash vapor fraction comprising some of the methyl acetate, methyl iodide, acetic acid, water, methanol and propionic acid precursors in the introduced liquid reaction composition, is separated from a preliminary flash liquid fraction comprising the remaining components. The preliminary flash vapor fraction is recycled to the carbonylation reactor. The preliminary flash liquid fraction is introduced to the flash zone of the present invention with or without the addition of heat, in the same way as if the preliminary flash zone had not been used. In this embodiment, the preliminary flash zone is preferably operated at a pressure below that of the reactor, typically at a pressure of 3 to 9 bar-a and the flash zone is operated at a pressure below that of the preliminary flash zone, typically at a pressure of 1 to 4 bar-a. Preferably, the preliminary flash zone is maintained at a temperature of 120 to 160° C. and the flash zone is maintained at a temperature of 100 to 140° C.

It is important that any process stream containing iridium carbonylation catalyst which is to be recycled to the carbonylation reactor contains a water concentration of at least 0.5% by weight to stabilize the iridium catalyst.

Unlike the '535 patent, in the integrated process of the present invention, the carbonylation reaction conditions may or may not be selected to give an acetic acid process stream containing less than 400 ppm propionic acid and less than 1500 ppm water.

B. Rhodium-Catalyzed Process for Forming Mixed Acid Feed

With respect to the Monsanto process for forming acetic acid, conventional high water content rhodium catalyzed processes for forming acetic acid may form a crude acetic acid prior to entering a heavy ends column comprising on the order of from 1200 to 2000 wppm propionic acid. See, e.g., J. Jones, *Platinum Metals Review*, Vol. 44, No. 3, p. 94-104 (July 2000), incorporated by reference herein in its entirety. More recently, U.S. Pat. Nos. 5,001,259; 5,026,908; and 5,599,976, also incorporated herein in by reference in their entireties, indicate that at lower water concentrations, e.g., less than 8 wt. % water, optionally less than 5 wt. % water, from 1 to 4 wt. % water, or from 3 to 4 wt. % water, the carbonylation of methanol with a rhodium catalyst results in a great reduction (by an order of magnitude) in the rate of formation of byproduct propionic acid, although even the low water rhodium process may form a minor amount of propionic acid. The integrated process of the present invention advantageously may be adopted with either the high water (greater than 8 wt. % water) or low water rhodium-catalyzed carbonylation process.

Some conventional carbonylation processes yield acetic acid product comprising less than 1500 wppm propionic acid, e.g., less than 500 wppm propionic acid, or less than 100 wppm propionic acid. This product typically requires an energy intensive dehydration step and/or heavy ends removal step to achieve these low propionic acid levels. Embodiments of the present invention beneficially may eliminate either or both the heavy ends removal step and/or the dehydration step, allowing the carbonylation process to run at reduced operating conditions, e.g., lower energy requirements. Advantageously the present invention achieves an improvement in integration by allowing more propionic acid to be present in the acetic acid.

When a rhodium catalyst is utilized, the rhodium catalyst may be added in any suitable form such that the active rhodium catalyst is a carbonyl iodide complex. Exemplary rhodium catalysts are described in Michael Gauβ, et al., *Applied Homogeneous Catalysis with Organometallic Compounds: A Comprehensive Handbook in Two Volume*, Chapter 2.1, p. 27-200, (1$^{st}$ ed., 1996). Iodide salts optionally maintained in the reaction mixtures of the processes described herein may be in the form of a soluble salt of an alkali metal or alkaline earth metal or a quaternary ammonium or phosphonium salt. In certain embodiments, a catalyst co-promoter comprising lithium iodide, lithium acetate, or mixtures thereof may be employed. The salt co-promoter may be added as a non-iodide salt that will generate an iodide salt. The iodide catalyst stabilizer may be introduced directly into the reaction system. Alternatively, the iodide salt may be generated in-situ since under the operating conditions of the reaction system, a wide range of non-iodide salt precursors will react with methyl iodide or hydroiodic acid in the reaction medium to generate the corresponding co-promoter iodide salt stabilizer. For additional detail regarding rhodium catalysis and iodide salt generation, see U.S. Pat. Nos. 5,001,259; 5,026,908; and 5,144,068, which are hereby incorporated by reference.

A halogen co-catalyst/promoter is generally used in combination with the Group VIII metal catalyst component. Methyl iodide is a preferred halogen promoter. Preferably, the concentration of halogen promoter in the reaction medium ranges from 1 wt. % to 50 wt. %, and preferably from 2 wt. % to 30 wt. %.

The halogen promoter may be combined with the salt stabilizer/co-promoter compound. Particularly preferred are iodide or acetate salts, e.g., lithium iodide or lithium acetate.

Other promoters and co-promoters may be used as part of the catalytic system of the present invention as described in U.S. Pat. No. 5,877,348, which is hereby incorporated by reference. Suitable promoters are selected from ruthenium, osmium, tungsten, rhenium, zinc, cadmium, indium, gallium, mercury, nickel, platinum, vanadium, titanium, copper, aluminum, tin, antimony, and are more preferably selected from ruthenium and osmium. Specific co-promoters are described in U.S. Pat. No. 6,627,770, which is incorporated herein by reference.

A promoter may be present in an effective amount up to the limit of its solubility in the liquid reaction composition and/or any liquid process streams recycled to the carbonylation reactor from the acetic acid recovery stage. When used, the promoter is suitably present in the liquid reaction composition at a molar ratio of promoter to metal catalyst of 0.5:1 to 15:1, preferably 2:1 to 10:1, more preferably 2:1 to 7.5:1. A suitable promoter concentration is 400 to 5000 ppm.

In one embodiment, the temperature of the carbonylation reaction in the reactor is preferably from 150° C. to 250° C., e.g., from 150° C. to 225° C., or from 150° C. to 200° C. The pressure of the carbonylation reaction is preferably from 1 to 20 MPa, preferably 1 to 10 MPa, most preferably 1.5 to 5 MPa Acetic acid is typically manufactured in a liquid phase reaction at a temperature from about 150° C. to about 200° C. and a total pressure from about 2 to about 5 MPa.

In one embodiment, the reaction mixture comprises a reaction solvent or mixture of solvents. The solvent is preferably compatible with the catalyst system and may include pure alcohols, mixtures of an alcohol feedstock, and/or the desired carboxylic acid and/or esters of these two compounds. In one embodiment, the solvent and liquid reaction medium for the (low water) carbonylation process is preferably acetic acid.

Water may be formed in situ in the reaction medium, for example, by the esterification reaction between methanol reactant and acetic acid product. In some embodiments, water is introduced to reactor together with or separately from other components of the reaction medium. Water may be separated from the other components of reaction product withdrawn from reactor and may be recycled in controlled amounts to maintain the required concentration of water in the reaction medium. Preferably, the concentration of water maintained in the reaction medium ranges from 0.1 wt. % to 16 wt. %, e.g., from 1 wt. % to 14 wt. %, or from 1 wt. % to 3 wt. % of the total weight of the reaction product.

The desired reaction rates are obtained even at low water concentrations by maintaining in the reaction medium an ester of the desired carboxylic acid and an alcohol, desirably the alcohol used in the carbonylation, and an additional iodide ion that is over and above the iodide ion that is present as hydrogen iodide. An example of a preferred ester is methyl acetate. The additional iodide ion is desirably an iodide salt, with lithium iodide (LiI) being preferred. It has been found, as described in U.S. Pat. No. 5,001,259, that under low water concentrations, methyl acetate and lithium iodide act as rate promoters only when relatively high concentrations of each of these components are present and that the promotion is higher when both of these components are present simultaneously. The absolute concentration of iodide ion content is not a limitation on the usefulness of the present invention.

In low water carbonylation, the additional iodide over and above the organic iodide promoter may be present in the catalyst solution in amounts ranging from 2 wt. % to 20 wt. %, e.g., from 2 wt. % to 15 wt. %, or from 3 wt. % to 10 wt. %; the methyl acetate may be present in amounts ranging from 0.5 wt % to 30 wt. %, e.g., from 1 wt. % to 25 wt. %, or from 2 wt. % to 20 wt. %; and the lithium iodide may be present in amounts ranging from 5 wt. % to 20 wt %, e.g., from 5 wt. % to 15 wt. %, or from 5 wt. % to 10 wt. %. The catalyst may be present in the catalyst solution in amounts ranging from 200 wppm to 2000 wppm, e.g., from 200 wppm to 1500 wppm, or from 500 wppm to 1500 wppm.

In one embodiment, carbon monoxide is reacted with methanol in a suitable reactor, e.g., a continuous stirred tank reactor ("CSTR") or a bubble column reactor. Preferably, the carbonylation process is a low water, catalyzed, e.g., rhodium-catalyzed, carbonylation of methanol to acetic acid, as exemplified in U.S. Pat. No. 5,001,259, which is hereby incorporated by reference.

Hydrogenation Process

Regardless of how formed, according to the integrated process of the invention, the mixed acid feed comprising acetic acid and one or more higher alcohols is sent to a hydrogenation reactor for conversion thereof to ethanol and one or more higher alcohols. Suitable hydrogenation catalysts for the hydrogenation reaction include catalysts comprising a first metal and optionally one or more of a second metal, a third metal or additional metals, optionally on a catalyst support. The first and optional second and third metals may be selected from Group IB, IIB, IIIB, IVB, VB, VIIB, VIIB, VIII transitional metals, a lanthanide metal, an actinide metal or a metal selected from any of Groups IIIA, IVA, VA, and VIA. Preferred metal combinations for some exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, silver/palladium, copper/palladium, nickel/palladium, gold/palladium, ruthenium/rhenium, and ruthenium/iron. Exemplary catalysts are further described in U.S. Pat. No. 7,608,744 and U.S. Publication Nos. 2010/0029995 and 2010/0197485, the entireties of which are incorporated herein by reference.

In one exemplary embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium. More preferably, the first metal is selected from platinum and palladium. When the first metal comprises platinum, it is preferred that the catalyst comprises platinum in an amount less than 5 wt. %, e.g., less than 3 wt. % or less than 1 wt. %, due to the high demand for platinum.

As indicated above, the catalyst optionally further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel. More preferably, the second metal is selected from tin and rhenium.

If the catalyst includes two or more metals, e.g., a first metal and a second metal, the first metal optionally is present in the catalyst in an amount from 0.1 wt. % to 10 wt. %, e.g., from 0.1 wt. % to 5 wt. %, or from 0.1 wt. % to 3 wt. %. The second metal preferably is present in an amount from 0.1 wt. % and 20 wt. %, e.g., from 0.1 wt. % to 10 wt. %, or from 0.1 wt. % to 5 wt. %. For catalysts comprising two or more metals, the two or more metals may be alloyed with one another or may comprise a non-alloyed metal solution or mixture. Thus, in one embodiment, the catalyst is substantially free of alloys. In one embodiment, where the catalyst comprises a first metal that is a Group VIII noble metal, the catalyst may be substantially free of any additional metals capable of alloying with the Group VIII noble metal, e.g., containing less than 10 wppm, less than 1 wppm or less than 0.1 wppm of such second metals.

The preferred metal ratios may vary depending on the metals used in the catalyst. In some exemplary embodiments, the mole ratio of the first metal to the second metal is from 10:1 to 1:10, e.g., from 4:1 to 1:4, from 2:1 to 1:2, from 1.5:1 to 1:1.5 or from 1.1:1 to 1:1.1.

The catalyst may also comprise a third metal selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. It should be noted, however, that in some embodiments, the catalyst is substantially free of rhenium meaning that it contains less than 10 wppm rhenium, less than 1 wppm or less than 0.1 wppm. In another aspect, the catalyst is substantially free of rhenium, tungsten and molybdenum, e.g., containing less than 10 wppm rhenium, less than 1 wppm or less than 0.1 wppm of such metals, individually or collectively. More preferably, the third metal is selected from cobalt, palladium, and ruthenium. When present, the total weight of the third metal preferably is from 0.05 wt. % and 4 wt. %, e.g., from 0.1 wt. % to 3 wt. %, or from 0.1 wt. % to 2 wt. %.

In addition to one or more metals, the exemplary catalysts further comprise a support or a modified support, meaning a support that includes a support material and a support modifier, which adjusts the acidity of the support material. The total weight of the support or modified support, based on the total weight of the catalyst, preferably is from 75 wt. % to 99.9 wt. %, e.g., from 78 wt. % to 97 wt. %, or from 80 wt. % to 95 wt. %. In preferred embodiments that use a modified support, the support modifier is present in an amount from 0.1 wt. % to 50 wt. %, e.g., from 0.2 wt. % to 25 wt. %, from 0.5 wt. % to 15 wt. %, or from 1 wt. % to 8 wt. %, based on the total weight of the catalyst.

Suitable support materials may include, for example, stable metal oxide-based supports or ceramic-based supports. Preferred supports include silicaceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

In the production of ethanol, the catalyst support may be modified with a support modifier. Preferably, the support modifier is a basic modifier that has a low volatility or no volatility. Such basic modifiers, for example, may be selected from the group consisting of: (i) alkaline earth oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. Preferably, the support modifier is selected from the group consisting of oxides and metasilicates of any of sodium, potassium, magnesium, calcium, scandium, yttrium, and zinc, as well as mixtures of any of the foregoing. Preferably, the support modifier is a calcium silicate, and more preferably calcium metasilicate ($CaSiO_3$). If the support modifier comprises calcium metasilicate, it is preferred that at least a portion of the calcium metasilicate is in crystalline form.

A preferred silica support material is SS61138 High Surface Area (HSA) Silica Catalyst Carrier from Saint Gobain NorPro. The Saint-Gobain NorPro SS61138 silica contains approximately 95 wt. % high surface area silica; a surface area of about 250 $m^2/g$; a median pore diameter of about 12 nm; an average pore volume of about 1.0 $cm^3/g$ as measured by mercury intrusion porosimetry and a packing density of about 0.352 $g/cm^3$ (22 $lb/ft^3$).

A preferred silica/alumina support material is KA-160 (Sud Chemie) silica spheres having a nominal diameter of about 5 mm, a density of about 0.562 g/ml, in absorptivity of about 0.583 g $H_2O$/g support, a surface area of about 160 to 175 $m^2/g$, and a pore volume of about 0.68 ml/g.

As will be appreciated by those of ordinary skill in the art, support materials are selected such that the catalyst system is suitably active, selective and robust under the process conditions employed for the formation of ethanol.

The metals of the catalysts may be dispersed throughout the support, coated on the outer surface of the support (egg shell) or decorated on the surface of the support.

The catalyst compositions suitable for use with the present invention preferably are formed through metal impregnation of the modified support, although other processes such as chemical vapor deposition may also be employed. Such impregnation techniques are described in U.S. Pat. No. 7,608,744, U.S. Publication No. 2010/0029995, and U.S. application Ser. No. 12/698,968, referred to above, the entireties of which are incorporated herein by reference.

Some embodiments of the process of hydrogenating a mixed acid feed to form ethanol and one or more higher alcohols according to one embodiment of the invention may include a variety of configurations using a fixed bed reactor or a fluidized bed reactor, as one of skill in the art will readily appreciate. In many embodiments of the present invention, an "adiabatic" reactor can be used; that is, there is little or no need for internal plumbing through the reaction zone to add or remove heat. In other embodiments, radial flow reactor or reactors may be employed, or a series of reactors may be employed with or with out heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 KPa to 3000 KPa (about 1.5 to 435 psi), e.g., from 50 KPa to 2300 KPa, or from 100 KPa to 1500 KPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

Although the reaction consumes two moles of hydrogen per mole of acid to produce one mole of ethanol (or higher alcohol for the higher acids), the actual molar ratio of hydrogen to total acid (including acetic acid and higher acid) in the feed stream may vary from about 100:1 to 1:100, e.g., from 50:1 to 1:50, from 20:1 to 1:2, or from 12:1 to 1:1. Most preferably, the molar ratio of hydrogen to total acid is greater than 2:1, e.g., greater than 4:1 or greater than 8:1.

Contact or residence time can also vary widely, depending upon such variables as amount of acetic acid, amount of higher acid, catalyst, reactor, temperature and pressure. Typical contact times range from a fraction of a second to more than several hours when a catalyst system other than a fixed bed is used, with preferred contact times, at least for vapor phase reactions, of from 0.1 to 100 seconds, e.g., from 0.3 to 80 seconds or from 0.4 to 30 seconds.

As indicated above, the feed stream that is fed to the hydrogenation reaction comprises acetic acid and one or more higher acids, e.g., propionic acid. For example, the acid feed stream may comprise a higher acid, e.g., such as propionic acid, in an amount greater than 0.01 wt. %, e.g., greater than 0.04 wt. %, greater than 0.08 wt. %, greater than 1 wt. %, greater than 2 wt. % or greater than 5 wt. %. In terms of ranges, the mixed acid feed stream may comprise the higher acid in an amount from 0.001 wt. % to 40 wt. %, e.g., from 0.01 wt. % 20 wt. %, from 0.04 wt. % to 20 wt. %, from 0.5 to 10 wt. %, from 1 to 8 wt. % or from 2 to 5 wt. %, or in other embodiments, in an amount ranging from 0.001 wt. % to 20 wt. %, e.g., from 0.001 wt. % to 15 wt. %, from 0.01 wt. % to 14 wt. %, from 0.13 wt. % to 13.2 wt. %, from 1.3 wt. % to 11.9 wt. %, or from 4 wt. % to 9.3 wt. %. In some exemplary embodiments, the molar ratio of acetic acid to the higher acids (collectively) in the feed stream ranges from 1:1 to 10,000:1, e.g., from 1:1 to 1000:1, from 1:1 to 200:1, from 2:1 to 150:1, from 10:1 to 120:1 or from 50:1 to 100:1. The feed stream may also comprise esters and/or anhydrides as well as acetaldehyde and acetone. Thus, the feed stream may be a cruder acetic acid feed stream, e.g., a less-refined acetic acid feed stream. In these embodiments, the propionic acid in the acetic acid feed stream is hydrogenated to form n-propanol, which may serve as a denaturant (e.g., for non-fuel uses). The n-propanol may be present in the resulting mixed alcohol composition in an amount ranging from 0.001 wt. % to 40 wt. %, e.g., from 0.01 wt. % 20 wt. %, from 0.04 wt. % to 20 wt. %, from 0.5 to 10 wt. %, from 1 to 8 wt. % or from 2 to 5 wt. %, or in other embodiments, in an amount ranging from 0.001 wt. % to 20 wt. %, e.g., from 0.001 wt. % to 15 wt. %, from 0.01 wt. % to 14 wt. %, from 0.13 wt. % to 13.2 wt. %, from 1.3 wt. % to 11.9 wt. %, or from 4 wt. % to 9.3 wt. %.

Alternatively, acetic acid and higher acids in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the ethanol synthesis reaction zones of the present invention without the need for condensing the acetic acid, the higher acid and light ends or removing water, saving overall processing costs.

In one embodiment, acetone is added to the reactor as a reactant in addition to the acetic acid, the higher acid and hydrogen. Without being bound by theory, it is believed that the addition of acetone to the reaction provides for the production of isopropanol, which may serve as a denaturant (e.g., for non-fuel uses) or enhance blending ability for fuel uses. In another aspect, acetone is formed as a by-product of the hydrogenation of acetic acid and the higher acid. Once formed, the acetone may be hydrogenated to form isopropanol. In some embodiments, where the presence of isopropanol is desired, e.g., as a denaturant, separate catalysts may be utilized to yield a higher concentration of acetone, which, upon subsequent hydrogenation, would result in a higher concentration of isopropanol in the crude ethanol composition. As an example, a catalyst composition comprising a support such as $TiO_2$, $ZrO_2$, $Fe_2O_3$, or $CeO_2$ may be used. Other exemplary catalyst compositions include ruthenium supported by $SiO_2$, iron supported by carbon, or palladium supported by carbon.

In one embodiment, the acetone is formed in an auxiliary reaction performed in an auxiliary acetone reactor. As an example, acetic acid and optionally the higher acid may be reacted in the auxiliary reactor under conditions effective to form acetone, e.g., ketonization. The acetic acid and optional higher acid fed to the auxiliary reactor may be drawn from the mixed acid feed stream fed to the hydrogenation reactor. The auxiliary reactor may be of the types discussed above. For example, the auxiliary reactor may be a fixed bed reactor that has a catalyst disposed therein. Preferably, the auxiliary reactor is in the shape of a pipe or tube, where the reactants, typically in the vapor form, are passed over or through the catalyst, which is disposed in the pipe or tube. In some embodiments, the auxiliary reactor utilizes a catalyst that promotes ketonization and/or favors the production of acetone. As an example, the catalyst may comprise a basic catalyst, e.g., thorium oxide. In some embodiments, the acetone yielded by the auxiliary reactor is directed to the hydrogenation reactor as a reactant in addition to the acetic acid, the higher acid and the hydrogen.

The acetic acid and the higher acid may be vaporized at the reaction temperature, following which the vaporized mixed acid feed can be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid or the higher acid. In one embodiment the acid may be vaporized at the boiling point of the acid at the particular pressure, and then the vaporized acid may be further heated to the reactor inlet temperature. In another embodiment, the acetic acid and the heavier acid are transferred to the vapor state by passing hydrogen, recycle gas, another suitable gas, or mixtures thereof through the mixed acid feed at a temperature below the boiling point of the acids, thereby humidifying the carrier gas with acetic acid and heavier acid vapors, followed by heating the mixed vapors up to the reactor inlet temperature. Preferably, the acetic acid and the heavier acid are transferred to the vapor by passing hydrogen and/or recycle gas through the mixed acid feed at a temperature at or below 125° C., followed by heating of the combined gaseous stream to the reactor inlet temperature.

In particular, the hydrogenation of the acetic acid may achieve favorable conversion of acetic acid and favorable selectivity and productivity to ethanol. Similarly, the hydrogenation of higher acids may achieve favorable conversion, selectivity and productivity to higher alcohols. For purposes of the present invention, the term "conversion" refers to the amount of acetic acid in the feed that is converted to a compound other than acetic acid. Conversion is expressed as a mole percentage based on specified acid in the feed. The conversion may be at least 10%, e.g., at least 20%, at least 40%, at least 50%, at least 60%, at least 70% or at least 80%. Although catalysts that have high conversions are desirable, such as at least 80% or at least 90%, in some embodiments a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on the converted acid. It should be understood that each compound converted from the specified acid has an independent selectivity and that selectivity is independent from conversion. For example, if 50 mole % of the converted acetic acid is converted to ethanol, we refer to the ethanol selectivity as 50%. Preferably, the catalyst selectivity to ethoxylates is at least 60%, e.g., at least 70%, or at least 80%. As used herein, the term "ethoxylates" refers specifically to the compounds ethanol, acetaldehyde, and ethyl acetate. Preferably, the selectivity of acetic acid to ethanol is at least 80%, e.g., at least 85% or at least 88%. Similar selectivities may be achieved for the higher acid to the higher alcohol. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are not detectable. Formation of alkanes may be low, and ideally less than 2%, less than 1%, or less than 0.5% of the acetic acid and higher acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 200 grams of ethanol per kilogram catalyst per hour, e.g., at least 400 grams of ethanol per kilogram catalyst per hour or at least 600 grams of ethanol per kilogram catalyst per hour, is preferred. In terms of ranges, the productivity preferably is from 200 to 3,000 grams of ethanol per kilogram catalyst per hour, e.g., from 400 to 2,500 per kilogram catalyst per hour or from 600 to 2,000 per kilogram catalyst per hour.

In various embodiments, the crude ethanol product produced by the hydrogenation process, before any subsequent processing, such as purification and separation, will typically comprise unreacted acetic acid, unreacted higher acid, ethanol, one or more higher alcohols, and water. As used herein, the term "crude alcohol product" refers to any composition comprising from 5 wt. % to 70 wt. % ethanol and higher alcohols and from 5 wt. % to 35 wt. % water. In some exemplary embodiments, the crude alcohol product comprises ethanol and higher alcohols in an amount from 5 wt. % to 70 wt. %, e.g., from 10 wt. % to 60 wt. %, or from 15 wt. % to 50 wt. %, based on the total weight of the crude ethanol product. Preferably, the crude ethanol product comprises at least 10 wt. % ethanol, at least 15 wt. % ethanol, or at least 20 wt. % ethanol. The crude alcohol product preferably comprises the higher alcohol or alcohols in an amount greater than 0.01 wt. %, e.g., greater than 0.04 wt. %, greater than 0.5 wt. %, greater than 0.8 wt. %, greater than 1 wt. %, greater than 2 wt. %, greater than 3 wt. % or greater than 5 wt. %. In terms of ranges, the crude alcohol product optionally comprises the higher alcohol or alcohols in an amount from 0.01 to 20 wt. %, e.g., from 0.04 to 20 wt. %, from 0.5 to 10 wt. %, from 1 to 8 wt. % or from 2 to 5 wt. %. In some exemplary embodiments, the molar ratio of ethanol to the higher alcohol in the crude alcohol product optionally ranges from 1:1 to 1000:1, e.g., from 1:1 to 200:1, from 2:1 to 150:1, from 10:1 to 120:1 or from 50:1 to 100:1.

The crude alcohol product typically will further comprise unreacted acetic acid and unreacted higher acid, depending on conversion, for example, in an amount of less than 90 wt. %, e.g., less than 80 wt. % or less than 70 wt. %. In terms of ranges, the unreacted acetic acid and unreacted higher acid is optionally present in amounts from 0 to 90 wt. %, e.g., from 5 wt. % to 80 wt. %, from 15 wt. % to 70 wt. %, from 20 wt. % to 70 wt. % or from 25 wt. % to 65 wt. %. Where acetone is included as a reactant, the crude alcohol product may comprise from 0.01 wt. % to 10 wt. % isopropanol, e.g., from 0.1 wt. % to 10 wt %, from 1 wt. % to 9 wt. % or from 3 wt. % to 7 wt. %. In other embodiments, the crude alcohol product comprises from 0.01 wt. % to 20 wt. % diethyl ether, e.g., from 0.1 wt. % to 10 wt. %, from 1 wt. % to 9 wt. % or from 3 wt. % to 7 wt. %. As water is formed in the reaction process, the crude alcohol product will generally comprise water, for example, in amounts ranging from 5 wt. % to 35 wt. %, e.g., from 10 wt. % to 30 wt. % or from 10 wt. % to 26 wt. %. Ethyl acetate and higher esters, e.g., propyl acetate or ethyl propionate, may also be produced during the hydrogenation of acetic acid and higher acids or through side reactions. In these embodiments, the crude alcohol product may comprise esters in an amount ranging from 0 to 20 wt. %, e.g., from 0 to 15 wt. %, from 1 to 12 wt. % or from 3 to 10 wt. %. Acetaldehyde may also be produced through side reactions. Higher esters, such as propyl acetate and ethyl propionate, may be present in an amount from 0.001 to 5 wt. %, e.g., from 0.01 to 3 wt. % or from 0.1 to 1 wt. %. In these embodiments, the crude alcohol product comprises acetaldehyde in amounts ranging from 0 to 10 wt. %, e.g., from 0 to 3 wt. %, from 0.1 to 3 wt. % or from 0.2 to 2 wt. %. In some embodiments, where propionic acid is included as a reactant, the n-propanol formed via hydrogenation may be present in the crude alcohol product in an amount ranging from 0.001 wt. % to 40 wt. %, e.g., from 0.01 wt. % 20 wt. %, from 0.04 wt. % to 20 wt. %, from 0.5 to 10 wt. %, from 1 to 8 wt. % or from 2 to 5 wt. %, or in other embodiments, in an amount ranging from 0.001 wt. % to 20 wt. %, e.g., from 0.001 wt. % to 15 wt. %, from 0.01 wt. % to 14 wt. %, from 0.13 wt. % to 13.2 wt. %, from 1.3 wt. % to 11.9 wt. %, or from 4 wt. % to 9.3 wt. %.

Thus, the hydrogenation reaction produces a crude alcohol product that may comprise, inter alia, denaturants such as n-propanol, isopropanol, alkyl acetates such as ethyl acetate, diethyl ether, and/or acetaldehyde. Each of these in situ-formed compounds, alone or in combination with one another, may serve as a denaturant in a denatured ethanol composition. In some embodiments, all or a portion of the crude alcohol product may be combined with a purified ethanol stream to form a denatured ethanol composition. It is within the scope of the invention to adjust the reaction parameters to achieve desired crude alcohol product and, thus, a desired denatured ethanol composition. In one embodiment, the amount of reactants, e.g., acetic acid, higher acid (e.g., propionic acid), acetone, etc., fed to the hydrogenation reactor may be adjusted so as to achieve a specific amount of one or more components, e.g., denaturants, in the crude alcohol product. The denaturant, thus produced, may be combined with a purified ethanol stream to form a denatured ethanol composition. For example, a denatured ethanol composition comprising about 5 parts isopropanol to 100 parts ethanol, may be produced by feeding an acetic acid stream comprising acetic acid and acetone. As another example, a denatured ethanol composition comprising about 5 parts n-propanol to 100 parts ethanol, may be produced by feeding an acetic acid stream comprising acetic acid and propionic acid. It is further within the scope of the invention to adjust additional hydrogenation reactor parameters to achieve a crude alcohol product comprising a desired amount of a particular denaturant or combination of denaturants. For example, in order to produce a crude alcohol product comprising about 10 parts diethyl ether, a hydrogenation catalyst having an acidic support may be utilized as described in co-pending U.S. application Ser. No. 12/850,414, entitled "Processes for Making Diethyl Ether from Acetic Acid," filed on Aug. 4, 2010, the entire contents and disclosure of which is hereby incorporated by reference.

In one embodiment, because it is difficult to separate propanol, e.g., isopropanol or n-propanol, and ethanol from one another, all or a portion of the propanol formed in the hydrogenation reaction may follow the ethanol through the separation scheme. Because the crude ethanol composition, as formed, may contain in situ-formed denaturant(s), at least a portion of the crude ethanol composition, with or without further separation, may be combined with a purified ethanol stream to form a denatured ethanol composition. In one embodiment, one or more of the in situ-formed denaturants may be separated from the crude alcohol product and combined with a purified ethanol stream. In other embodiments, at least a portion, e.g., an aliquot portion, of the crude alcohol product may be combined with a purified ethanol stream. For example, when the crude alcohol product comprises n-propanol, at least a portion of an n-propanol-containing crude alcohol product may be combined with a purified ethanol stream to form a denatured ethanol composition comprising an n-propanol denaturant. In another embodiment, at least a portion of the n-propanol is separated from the crude alcohol product and combined with a purified ethanol stream to form an n-propanol denatured ethanol composition.

Other components, such as, for example, esters, ethers, aldehydes, ketones, alkanes, and carbon dioxide, if detectable, collectively may be present in amounts less than 10 wt. %, e.g., less than 6 wt. %, or less than 4 wt. %. In terms of ranges, the crude alcohol product composition may comprise the other components in an amount from 0.1 wt. % to 10 wt. %, e.g., from 0.1 wt. % to 6 wt. %, or from 0.1 wt. % to 4 wt. %. Exemplary crude alcohol product compositional ranges are provided in Table 1.

TABLE 1

CRUDE ALCOHOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 70 | 10 to 60 | 15 to 50 | 25 to 50 |
| Acetic Acid | 0 to 90 | 5 to 80 | 15 to 70 | 20 to 70 |
| Higher Alcohol* | 0.01 to 20 | 0.04 to 20 | 1 to 8 | 2 to 5 |
| Higher Acid** | <20 | 0.04 to 20 | 1 to 8 | 2 to 5 |
| Water | 5 to 35 | 5 to 30 | 10 to 30 | 10 to 26 |

TABLE 1-continued

CRUDE ALCOHOL PRODUCT COMPOSITIONS

| Component | Conc. (wt. %) | Conc. (wt. %) | Conc. (wt. %) | Conc. (wt. %) |
|---|---|---|---|---|
| Ethyl Acetate | 0 to 20 | 0 to 15 | 1 to 12 | 3 to 10 |
| Acetaldehyde | 0 to 10 | 0 to 3 | 0.1 to 3 | 0.2 to 2 |
| Others | 0.1 to 10 | 0.1 to 6 | 0.1 to 4 | — |

*preferably propanol (n-propanol, isopropanol or both).
**preferably propionic acid.

In one embodiment, the crude alcohol product may comprise acetic acid in an amount less than 20 wt. %, e.g., less than 15 wt. %, less than 10 wt. % or less than 5 wt. %. In embodiments having lower amounts of acetic acid, the conversion of acetic acid is preferably greater than 75%, e.g., greater than 85% or greater than 90%. In addition, the selectivity to alcohols may also be preferably high, and is preferably greater than 75%, e.g., greater than 85% or greater than 90%.

As shown in Table 1, in some embodiments the crude alcohol product may be a denatured ethanol composition. For example, the crude ethanol composition may comprise ethanol and at least one denaturant, which preferably comprises one or more higher alcohols, preferably propanol. In other aspects, in addition to or as an alternative to the higher alcohol(s), acetic acid, ethyl acetate, or acetaldehyde may be the denaturant. In other embodiments, the crude ethanol composition may be a denatured ethanol composition comprising at least one of the denaturants discussed above.

Integrated Processes

Figure 4:
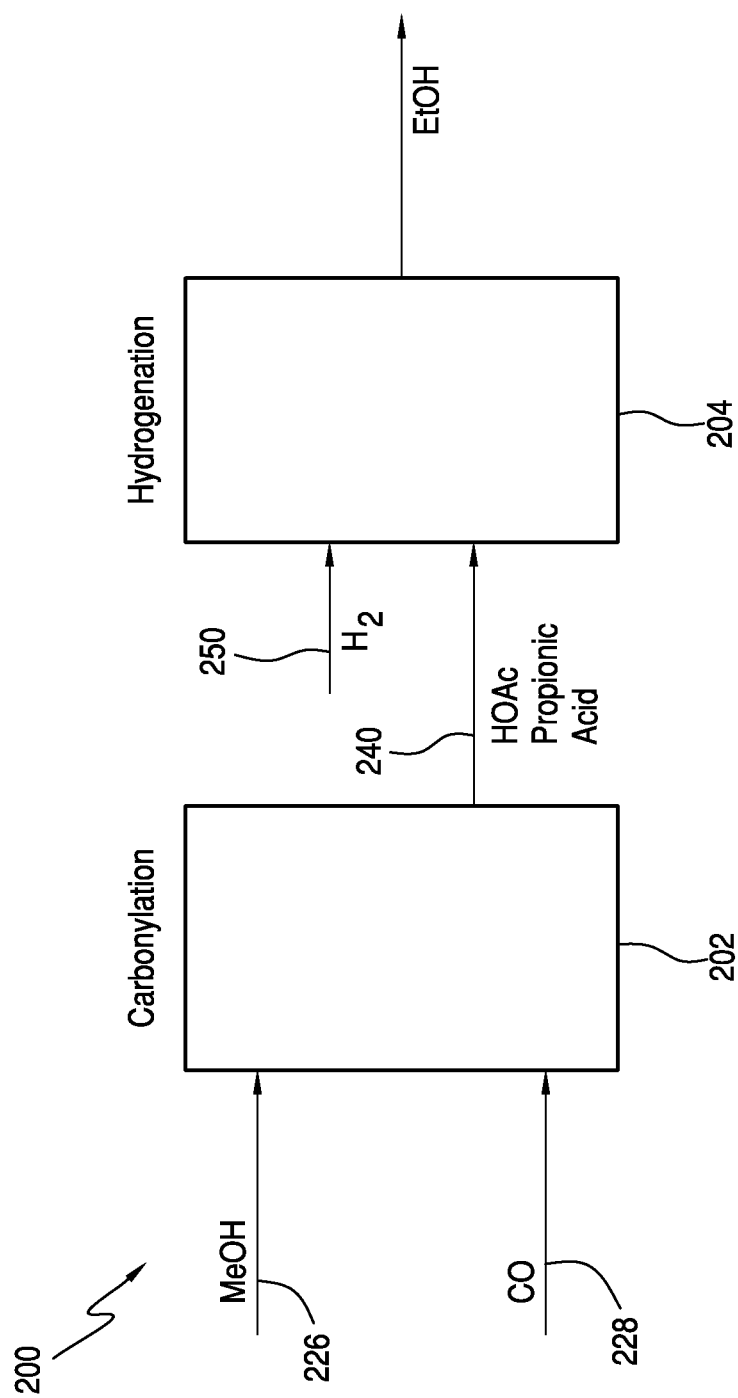
FIG. 4 is a schematic diagram of an integrated process according to one embodiment of the invention.

FIG. 4 is a diagram of an integrated process 200 in accordance with the present invention. Process 200 comprises carbonylation system 202 and hydrogenation system 204. Carbonylation system 202 receives methanol feed 226 and carbon monoxide feed 228. The methanol and the carbon monoxide are reacted in carbonylation zone 202 to form an crude product comprising acetic acid and water. A flasher may be used to remove residual catalyst from the crude product. Carbonylation system 202, in some embodiments, further comprises a purification train comprising one or more distillation column (not shown in FIG. 1) to separate crude product into an acetic acid product stream 240 comprising acetic acid and propionic acid, e.g., in an amount greater than 0.01 wt. %, greater than 0.04 wt. %, greater than 0.05 wt. %, greater than 0.08 wt. %, greater than 1 wt. % or greater than 2 wt. %. Acetic acid product stream 240 may further comprise water, e.g., in an amount from 0.15 wt. % to 25 wt. %. Preferably, the separation train includes the flasher and no more than one separation column, e.g., a light ends column.

Acetic acid product stream 240 is fed, more preferably directly fed, to hydrogenation system 204. Hydrogenation system 204 also receives hydrogen feed 250. In hydrogenation system 204, the acetic acid in acetic acid product stream (a mixed acid feed) is hydrogenated to form a crude alcohol product comprising ethanol and other compounds such as water, ethyl acetate, and unreacted acetic acid. In addition, the crude alcohol product further comprises propanol formed from the hydrogenation of propionic acid contained in the mixed acid feed. Hydrogenation system 204 further comprises one or more separation units, e.g., distillation columns, for recovering either: (i) a mixed alcohol stream comprising ethanol and a heavier alcohol, e.g., propanol, from the crude alcohol product; or (ii) both a purified ethanol stream and a purified propanol stream from the crude alcohol product. As shown, an ethanol product stream is recovered from hydrogenation system 204.

Figure 5:
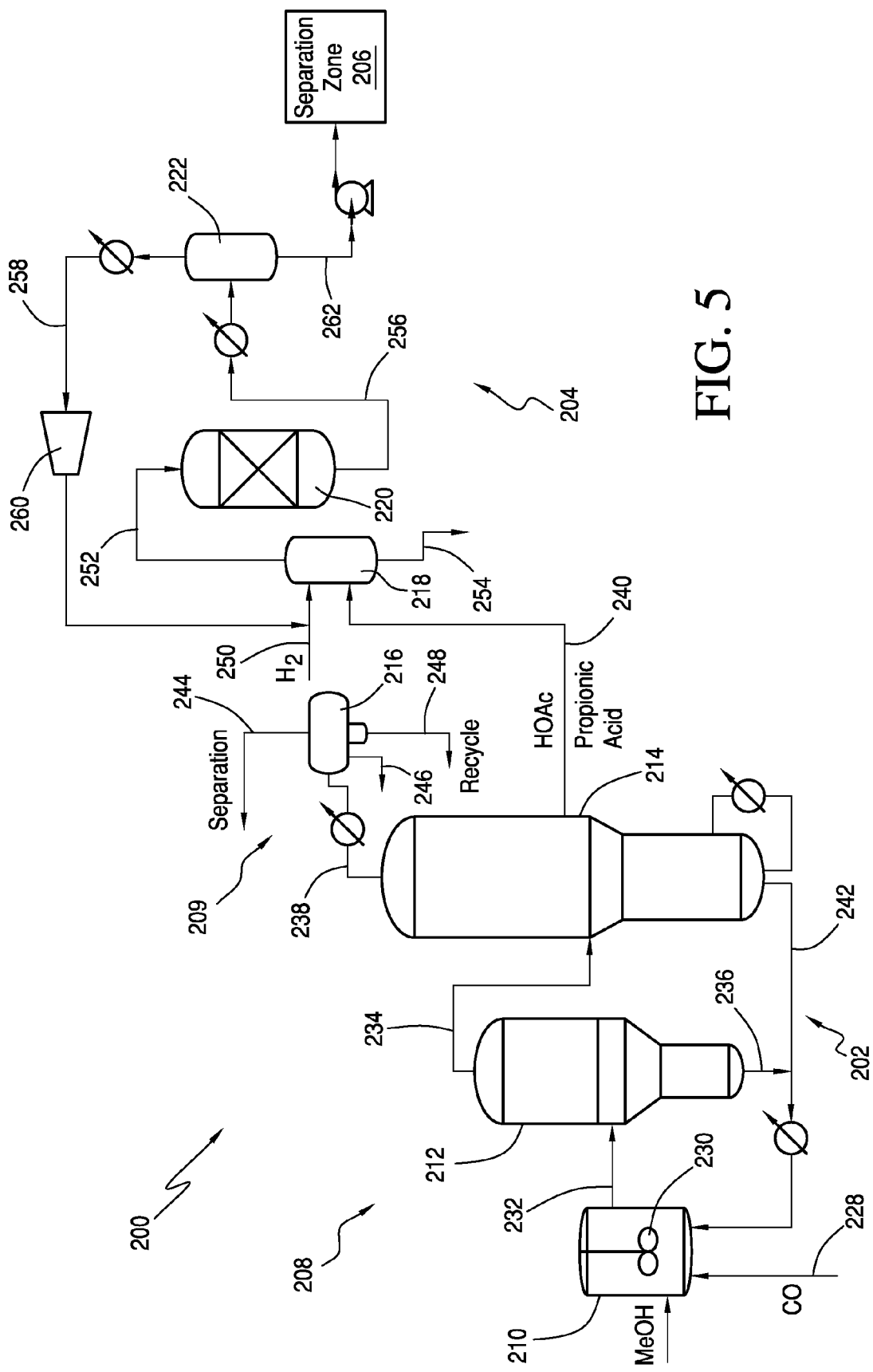
FIG. 5 is a schematic diagram of an integrated process according to one embodiment of the invention.

FIG. 5 shows exemplary integrated carbonylation and hydrogenation process 200, which comprises carbonylation system 202, hydrogenation zone 204, and hydrogenation separation zone 206. Carbonylation system 202 comprises: (1) reaction zone 208, which comprises carbonylation reactor 210 and flasher 212, and (2) carbonylation separation zone 209, which preferably comprises no more than one distillation column, e.g., a light ends column 214, and optionally a phase separator, e.g., decanter, 216. Hydrogenation zone 204 comprises vaporizer 218 and hydrogenation reactor 220. Hydrogenation separation zone 206 comprises one or more separation columns as described below with reference to FIGS. 1-3.

In carbonylation system 202, methanol feed stream 226 comprises methanol and/or reactive derivatives thereof and carbon monoxide 228 are fed to a lower portion of carbonylation reactor 210. Suitable reactive derivatives of methanol include methyl acetate, dimethyl ether, methyl formate, and mixtures thereof. The methanol stream that is sent to reactor 210 optionally comprises a minor amount of propanol, e.g., from 0.01 to 20 wt. %, from 0.04 to 20 wt. %, from 0.1 to 10 wt. % or from 0.5 to 10 wt. %, which may be carbonylated to form propionic acid in the resulting acetic acid product/feed. At least some of the methanol and/or reactive derivative thereof will be converted to, and hence present as, methyl acetate in the liquid reaction composition by reaction with acetic acid product or solvent. The concentration in the liquid reaction composition of methyl acetate is suitably in the range of from 0.5 wt. % to 70 wt. %, e.g., from 0.5 wt. % to 50 wt. %, from 1 wt. % to 35 wt. %, or from 1 wt. % to 20 wt. %.

Reactor 210 is preferably either a stirred vessel, e.g., CSTR, or bubble-column type vessel, with agitator 230 or without an agitator, within which the reaction medium is maintained, preferably automatically, at a predetermined level. This predetermined level may remain substantially constant during normal operation. Into reactor 210, methanol, carbon monoxide, and sufficient water may be continuously introduced as needed to maintain at least a finite concentration of water in the reaction medium. In one embodiment, carbon monoxide, e.g., in the gaseous state, is continuously introduced into reactor 210, desirably below agitator 230, which is used to stir the contents. The temperature of reactor 210 may be controlled, as indicated above. Carbon monoxide feed 228 is introduced at a rate sufficient to maintain the desired total reactor pressure.

The gaseous carbon monoxide feed is preferably thoroughly dispersed through the reaction medium by agitator 230. A gaseous purge is desirably vented via an off-gas line (not shown) from reactor 210 to prevent buildup of gaseous by-products, such as methane, carbon dioxide, and hydrogen, and to maintain a carbon monoxide partial pressure at a given total reactor pressure.

The crude acetic acid product is drawn off from the reactor 210 at a rate sufficient to maintain a constant level therein and is provided to flasher 212 via stream 232.

In flasher 212, the crude acetic acid product is separated in a flash separation step to obtain a volatile ("vapor") overhead stream 234 comprising acetic acid and a less volatile stream 236 comprising a catalyst-containing solution. The catalyst-containing solution comprises acetic acid containing the rhodium and the iodide salt along with lesser quantities of methyl acetate, methyl iodide, and water. The less volatile stream 236 preferably is recycled to reactor 210. Vapor overhead stream 234 also comprises methyl iodide, methyl acetate, water, and permanganate reducing compounds ("PRCs").

Overhead stream 234 from flasher 212 is directed to separation zone 209. Separation zone 209 comprises light ends column 214 and decanter 216. As discussed above, the separation zone 209 preferably includes no more than one separation column and optionally does not include a drying unit or a heavy ends column. In some embodiments, however, the separation zone 209 may include such additional columns so long as the resulting acetic acid composition comprises some heavier acid, e.g., propionic acid.

In light ends column 214, stream 234 yields a low-boiling overhead vapor stream 238, a purified acetic acid stream that preferably is removed via a sidestream 240, and a high boiling residue stream 242. Purified acetic acid that is removed via sidestream 240 preferably is conveyed, e.g., directly, without removing substantially any heavy acid, e.g., propionic acid, or optionally any water therefrom, to hydrogenation system 204. Thus, the present invention provides for production efficiencies by using an acetic acid stream having a higher propionic acid content than typical commercially available acetic acid, which beneficially reduces or eliminates the need for water removal downstream from light ends column 214 in carbonylation system 202.

In one embodiment, column 214 may comprise trays having different concentrations of water. In these cases, the composition of a withdrawn sidedraw may vary throughout the column. As such, the withdrawal tray may be selected based on the amount of propionic that is desired, e.g., greater than 0.01 wt. %, greater than 0.04 wt. %, or greater than 0.5 wt %. In another embodiment, the configuration of the column may be varied to achieve a desired amount or concentration of propionic acid and/or water in a sidedraw. Thus, an acetic acid feed may be produced, e.g., withdrawn from a column, having the a desired propionic acid and water content. Accordingly, in one embodiment, the invention is to a process for producing ethanol comprising the step of withdrawing a purified acetic acid sidedraw from a light ends column in a carbonylation process, wherein a location from which the sidedraw is withdrawn is based on a propionic acid and water content of the sidedraw. The side stream may comprise water in an amount from 0.15 wt. % to 25 wt. %. The process further comprises the steps of hydrogenating acetic acid and higher acid, e.g., propionic acid, in the resulting acid stream in the presence of a catalyst under conditions effective to form a crude alcohol product comprising ethanol, one or more higher alcohols, e.g., propanol, and water; and recovering the alcohols, in combination or separately, from the crude alcohol product.

The resulting acetic acid stream, in some embodiments, comprises methyl acetate, e.g., in an amount ranging from 0.01 wt. % to 10 wt. % or from 0.1 wt. % to 5 wt. %. This methyl acetate, in preferred embodiments, may be reduced to form methanol and/or ethanol. In addition to acetic acid, water, and methyl acetate, the purified acetic acid stream may comprise halogens, e.g., methyl iodide, which may be removed from the purified acetic acid stream.

Returning to column 214, low-boiling overhead vapor stream 238 is preferably condensed and directed to an overhead phase separation unit, as shown by overhead receiver decanter 216. Conditions are desirably maintained in the process such that low-boiling overhead vapor stream 238, once in decanter 216, will separate into a light phase and a heavy phase. Generally, low-boiling overhead vapor stream 238 is cooled to a temperature sufficient to condense and separate the condensable methyl iodide, methyl acetate, acetaldehyde and other carbonyl components, and water into two phases. A gaseous portion of stream 238 may include carbon monoxide, and other noncondensable gases such as methyl iodide, carbon dioxide, hydrogen, and the like and is vented from the decanter 216 via stream 244.

Condensed light phase 246 from decanter 216 preferably comprises water, acetic acid, higher acid, and permanganate reducing compounds ("PRCs"), as well as quantities of methyl iodide and methyl acetate. Condensed heavy phase 248 from decanter 216 will generally comprise methyl iodide, methyl acetate, and PRCs. The condensed heavy liquid phase 248, in some embodiments, will be recirculated, either directly or indirectly, to reactor 210. For example, a portion of condensed heavy liquid phase 248 can be recycled to reactor 210, with a slip stream (not shown), generally a small amount, e.g., from 5 to 40 vol. %, or from 5 to 20 vol. %, of the heavy liquid phase being directed to a PRC removal system. This slip stream of heavy liquid phase 248 may be treated individually or may be combined with condensed light liquid phase 246 for further distillation and extraction of carbonyl impurities in accordance with one embodiment of the present invention.

Acetic acid sidedraw 240 from distillation column 214 of carbonylation process 202 is preferably directed to hydrogenation system 204. In one embodiment, the acetic acid stream may be sidestream 240 from a light ends column 214.

In hydrogenation system 204, hydrogen feed line 250 and sidedraw 240 comprising acetic acid, higher acid and water is fed to vaporizer 218. Vapor feed stream 252 is withdrawn and fed to hydrogenation reactor 220. In one embodiment, lines 250 and 240 may be combined and jointly fed to the vaporizer 218. The temperature of vapor feed stream 252 is preferably from 100° C. to 350° C., e.g., from 120° C. to 310° C. or from 150° C. to 300° C. Vapor feed stream 252 comprises from 0.15 wt. % to 25 wt. % water. Any feed that is not vaporized is removed from vaporizer 218 via stream 254, as shown in FIG. 5, and may be recycled thereto or discarded. In addition, although FIG. 5 shows line 252 being directed to the top of reactor 220, line 252 may be directed to the side, upper portion, or bottom of reactor 220. Further modifications and additional components to reaction zone 204 are described below.

Reactor 220 contains the catalyst that is used in the hydrogenation of the carboxylic acid, preferably acetic acid. During the hydrogenation process, a crude alcohol product comprising ethanol and the higher alcohol is withdrawn, preferably continuously, from reactor 220 via line 256 and directed to flasher 222 and separation zone 206.

Figure 1B:
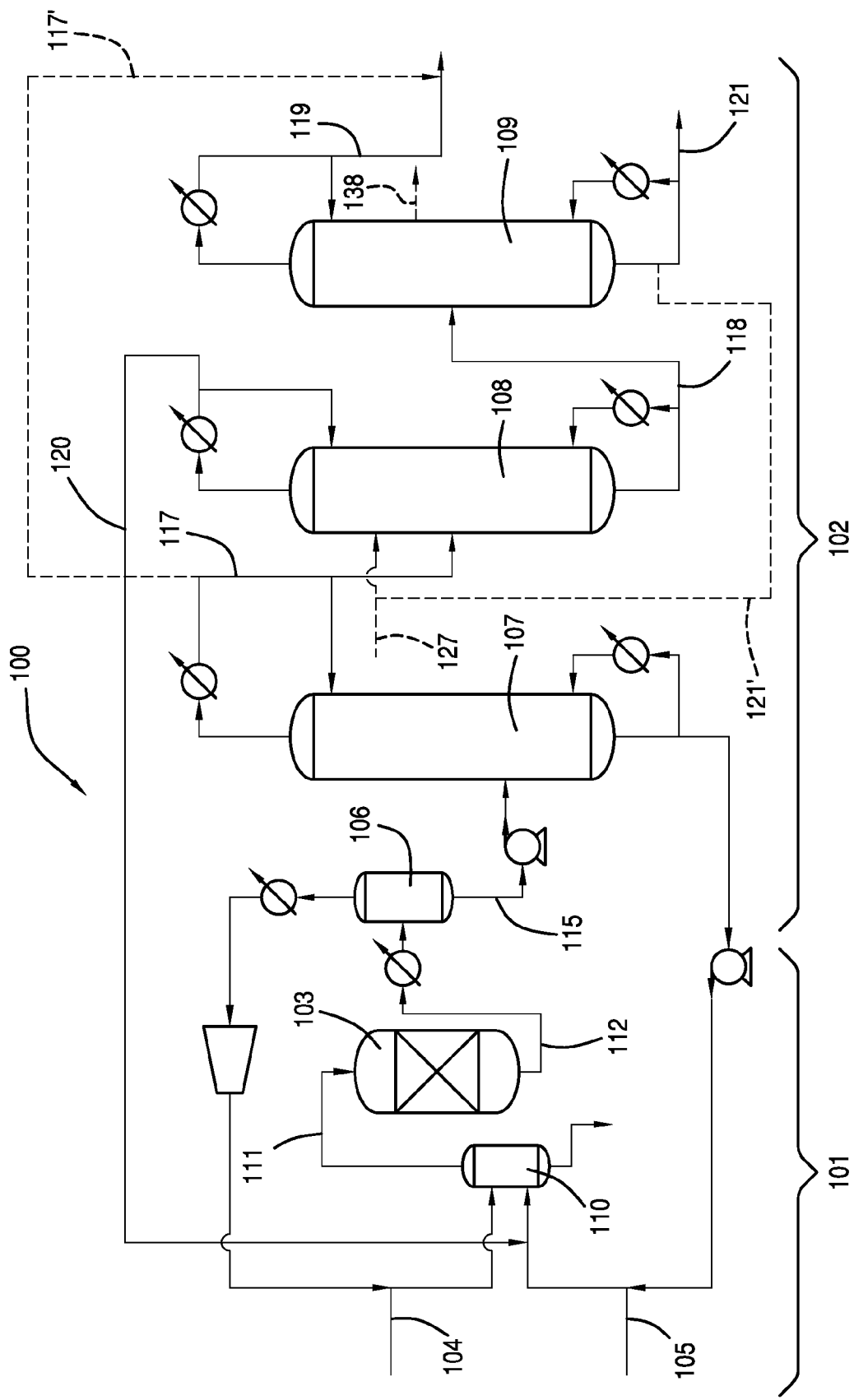
FIG. 1B is a schematic diagram of the system shown in FIG. 1A with a return of the distillate of a second column to the reactor zone.
Figure 1C:
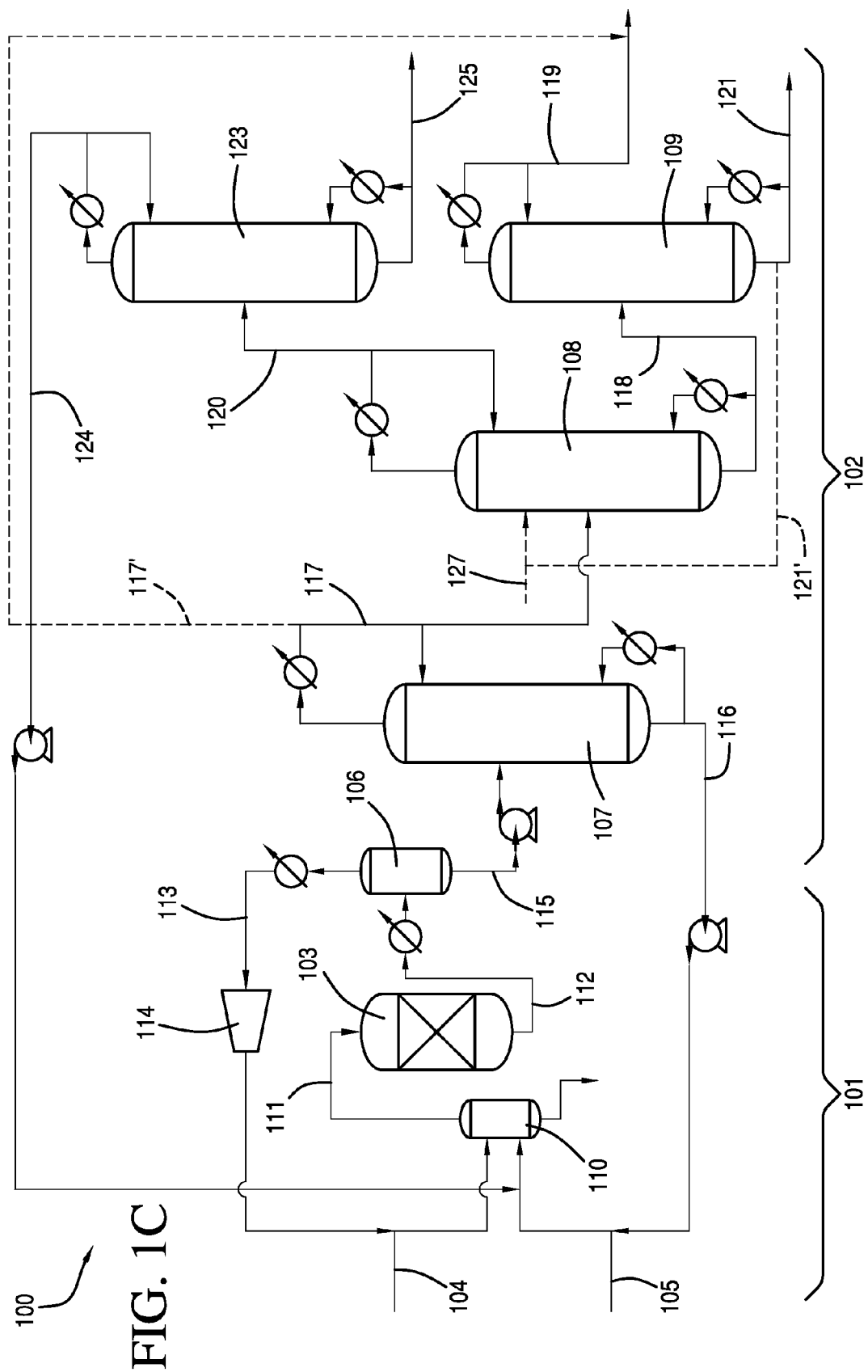
FIG. 1C is a schematic diagram of a hydrogenation system in accordance with one embodiment of the present invention.
Figure 2:
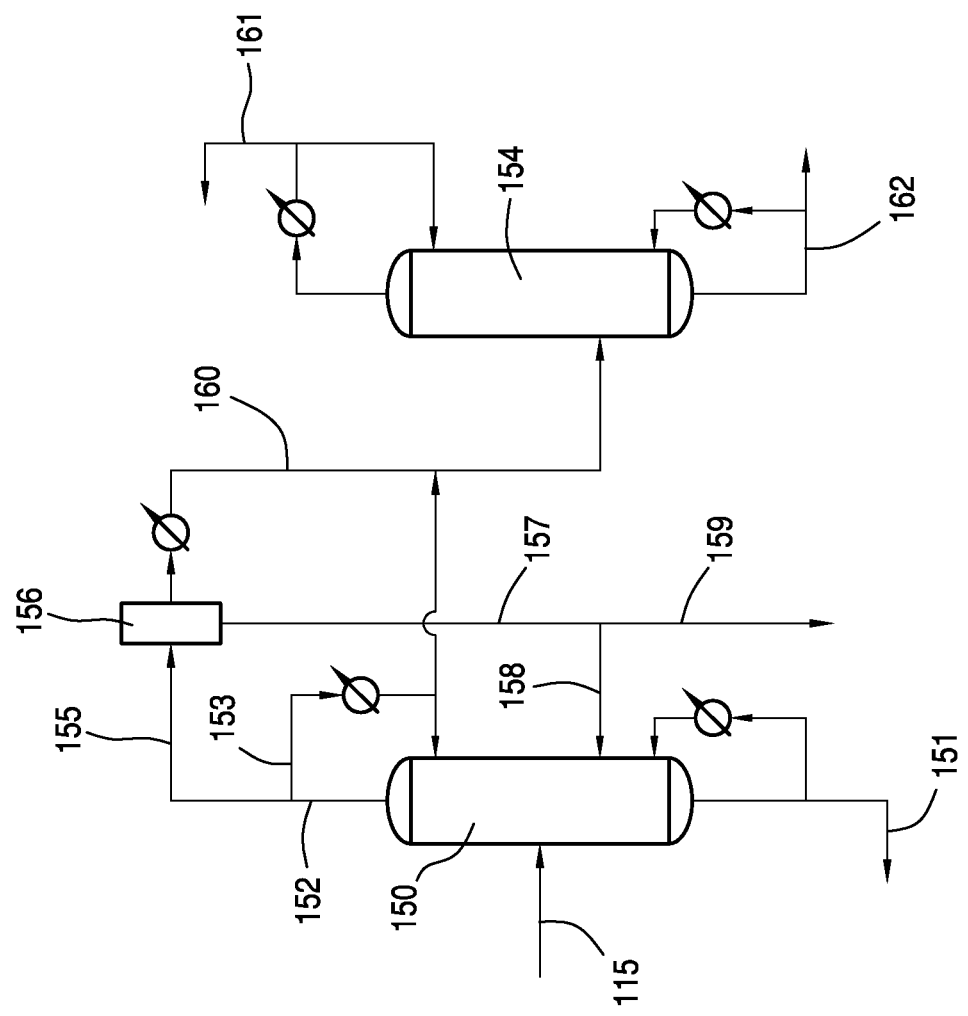
FIG. 2 is a schematic diagram of a separation scheme comprising two separation columns and a water separation unit in accordance with one embodiment of the present invention.
Figure 3:
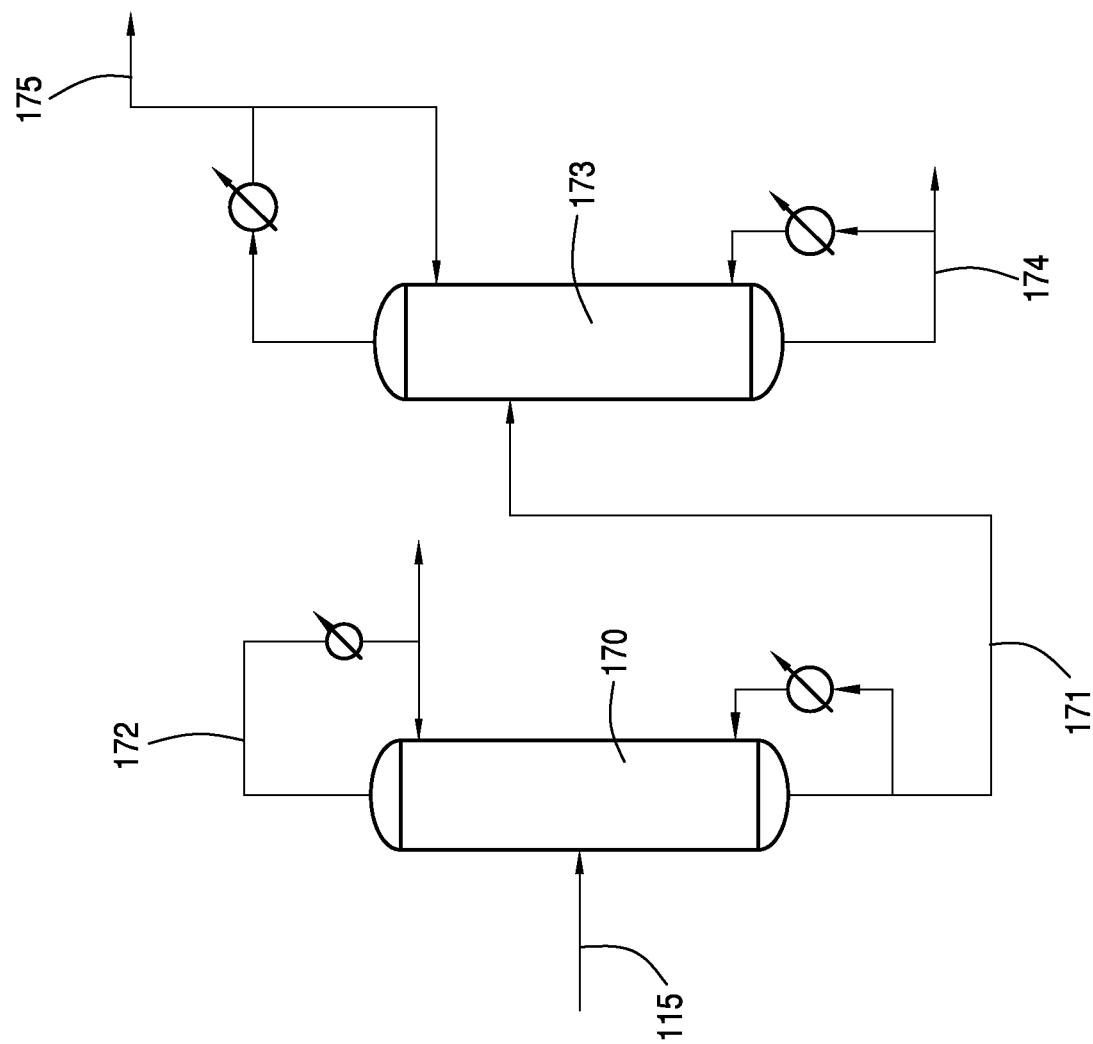
FIG. 3 is a schematic diagram of a separation scheme comprising two separation columns in accordance with one embodiment of the present invention.

The separation zone 206 comprises one or more separation columns as shown in FIGS. 1-3. The crude alcohol product may be condensed and fed to flasher 222, which, in turn, provides a vapor stream and a liquid stream. Flasher 222 may operate at a temperature of from 20° C. to 250° C., e.g., from 30° C. to 250° C. or from 60° C. to 200° C. The pressure of flasher 222 may be from 50 kPa to 2000 kPa, e.g., from 75 kPa to 1500 kPa or from 100 kPa to 1000 kPa.

The vapor stream exiting flasher 222 may comprise hydrogen and hydrocarbons, which may be purged and/or returned to reaction zone 204 via line 258. As shown in FIG. 5, the returned portion of the vapor stream passes through compressor 260 and is combined with the hydrogen feed and co-fed to vaporizer 218.

The liquid from flasher 222 is withdrawn and pumped as a feed composition via line 262 to the separation zone 206, as discussed below with reference to FIGS. 1-3. The contents of line 262 typically will be substantially similar to the product obtained directly from the reactor 220, and may, in fact, also be characterized as a crude ethanol product. However, the feed composition in line 262 preferably has substantially no hydrogen, carbon dioxide, methane or ethane, which are removed by flasher 222.

In some embodiments, some or all of the raw materials for the integrated process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884, 253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form syngas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into syngas, and U.S. Pat. No. 6,685,754, which discloses a method for the production of a hydrogen-containing gas composition, such as syngas including hydrogen and carbon monoxide, are incorporated herein by reference in their entireties.

Purification

FIG. 1A shows a hydrogenation system 100 suitable for the hydrogenation of acetic acid and higher acids and separating a mixed alcohol product from the crude reaction mixture according to one embodiment of the invention. System 100 comprises reaction zone 101 and distillation zone 102. Reaction zone 101 comprises reactor 103, hydrogen feed line 104 and feed line 105. As discussed above, a mixed acid feed comprising acetic acid and one or more heavier acids, e.g., propionic acid, is preferably fed to the reaction zone 101. The acetic acid and the one or more heavier acids may be fed separately or together to the reaction zone. In other embodiments, where acetone utilized as a reactant, reaction zone 101 further comprises an acetone feed line (not shown). In other embodiments, where the heavier acid is fed separately to as a reactant, reaction zone 101 may further comprise a heavier acid feed line, e.g., propionic acid feed line (not shown).

Distillation zone 102 comprises flasher 106, first column 107, second column 108, and third column 109. Hydrogen, acetic acid, the heavier acid(s) and optionally acetone are fed to a vaporizer 110 via lines 104 and 105, respectively, to create a vapor feed stream in line 111 that is directed to reactor 103. In one embodiment, lines 104 and 105 may be combined and jointly fed to the vaporizer 110, e.g., in one stream containing both hydrogen, acetic acid and the heavier acid. The temperature of the vapor feed stream in line 111 is preferably from 100° C. to 350° C., e.g., from 120° C. to 310° C. or from 150° C. to 300° C. Any feed that is not vaporized is removed from vaporizer 110, as shown in FIG. 1A, and may be recycled thereto. In addition, although FIG. 1A shows line 111 being directed to the top of reactor 103, line 111 may be directed to the side, upper portion, or bottom of reactor 103. Although one reactor and one flasher are shown in FIGS. 1A, 1B and 1C, additional reactors and/or components may be included in various optional embodiments of the present invention. For example, the hydrogenation system may optionally comprise dual reactors, dual flashers, heat exchanger(s), and/or pre-heater(s).

Reactor 103 contains the catalyst that is used in the hydrogenation of the carboxylic acid, preferably acetic acid and the heavier acid. In some embodiment where acetone is a reactant and isopropanol is a desired co-product with ethanol, the catalyst in reactor 103 is selected such that, in addition to ethanol, isopropanol is also produced, optionally in addition to one or more higher alcohols. As an example, a catalyst composition comprising a support such as $TiO_2$, $ZrO_2$, $Fe_2O_3$, or $CeO_2$ may be used. In some embodiments, these catalysts promote higher acetone formation. Other exemplary catalyst compositions include ruthenium supported by $SiO_2$, iron supported by carbon, or palladium supported by carbon. In other embodiments, the temperature of reactor 103 may be adjusted to achieve a desired higher alcohol, e.g., propanol, concentration. For example, maintaining the reaction temperature in a range of 200° C. to 350° C., e.g., from 225° C. to 300° C., may lead to an ethanol composition comprising from 0.1 wt. % to 10 wt. % isopropanol, e.g., from 1 wt. % to 9 wt. % or from 3 wt. % to 7 wt. %. In one embodiment, one or more guard beds (not shown) may be used to protect the catalyst from poisons or undesirable impurities contained in the feed or return/recycle streams. Such guard beds may be employed in the vapor or liquid streams. Suitable guard bed materials are known in the art and include, for example, carbon, silica, alumina, ceramic, or resins. In one aspect, the guard bed media is functionalized to trap particular species such as sulfur or halogens. During the hydrogenation process, a crude alcohol product stream is withdrawn, preferably continuously, from reactor 103 via line 112. The crude alcohol product stream may be condensed and fed to flasher 106, which, in turn, provides a vapor stream and a liquid stream. The flasher 106 in one embodiment preferably operates at a temperature of from 50° C. to 500° C., e.g., from 70° C. to 400° C. or from 100° C. to 350° C. In one embodiment, the pressure of flasher 106 preferably is from 50 KPa to 2000 KPa, e.g., from 75 KPa to 1500 KPa or from 100 to 1000 KPa. In one preferred embodiment, the temperature and pressure of flasher 106 is similar to the temperature and pressure of reactor 103.

The vapor stream exiting the flasher 106 may comprise hydrogen and hydrocarbons, which may be purged and/or returned to reaction zone 101 via line 113. As shown in FIG. 1A, the returned portion of the vapor stream passes through compressor 114 and is combined with the hydrogen feed and co-fed to vaporizer 110.

The liquid from flasher 106 is withdrawn and pumped as a feed composition via line 115 to the side of first column 107, also referred to as the acid separation column. The contents of line 115 typically will be substantially similar to the product obtained directly from the reactor, and may, in fact, also be characterized as a crude alcohol product. However, the feed composition in line 115 preferably has substantially no hydrogen, carbon dioxide, methane or ethane, which are removed by flasher 106. Exemplary components of liquid in line 115 are provided in Table 2. It should be understood that liquid line 115 may contain other components, not listed, such as components in the feed.

TABLE 2

FEED COMPOSITION TO FIRST DISTILLATION COLUMN

|  | Conc. (wt. %) | Conc. (wt. %) | Conc. (wt. %) |
|---|---|---|---|
| Ethanol | 5 to 70 | 10 to 60 | 15 to 50 |
| Higher Alcohols* | 0.01 to 20 | 0.04 to 20 | 0.5 to 10 |
| Water | 5 to 35 | 5 to 30 | 10 to 30 |
| Acetic Acid | <90 | 5 to 80 | 15 to 70 |
| Ethyl Acetate | <20 | 0.001 to 15 | 1 to 12 |
| Acetaldehyde | <10 | 0.001 to 3 | 0.1 to 3 |
| Acetal | <5 | 0.001 to 2 | 0.005 to 1 |
| Acetone | <5 | 0.0005 to 0.05 | 0.001 to 0.03 |
| Other Esters | <5 | <0.005 | <0.001 |
| Other Ethers | <5 | <0.005 | <0.001 |

The amounts indicated as less than (<) in the tables throughout present application are preferably not present and if present may be present in trace amounts or in amounts greater than 0.0001 wt. %.

The "other esters" in Table 2 may include, but are not limited to, ethyl propionate, methyl acetate, isopropyl acetate, n-propyl acetate, n-butyl acetate or mixtures thereof. The "other ethers" in Table 2 may include, but are not limited to, diethyl ether, methyl ethyl ether, isobutyl ethyl ether or mixtures thereof. The "higher alcohols" in Table 2 may include, but are not limited to, isopropanol, n-propanol, n-butanol or mixtures thereof.

When the acid content in line 115 is less than 5 wt. %, the acid separation column 107 may be skipped and line 115 may be introduced directly to second column 108, also referred to herein as a light ends column.

In the embodiment shown in FIG. 1A, line 115 is introduced in the lower part of first column 107, e.g., lower half or lower third. In first column 107, unreacted acids, a portion of the water, and other heavy components, if present, are removed from the composition in line 115 and are withdrawn, preferably continuously, as residue. Some or all of the residue may be returned and/or recycled back to reaction zone 101 via line 116. First column 107 also forms an overhead distillate, which is withdrawn in line 117, and which may be condensed and refluxed, for example, at a ratio of from 10:1 to 1:10, e.g., from 3:1 to 1:3 or from 1:2 to 2:1.

Any of columns 107, 108 or 109 may comprise any distillation column capable of separation and/or purification. The columns preferably comprise tray columns having from 1 to 150 trays, e.g., from 10 to 100 trays, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in two or more columns such that the vapor from the first section enters the second section while the liquid from the second section enters the first section, etc.

The associated condensers and liquid separation vessels that may be employed with each of the distillation columns may be of any conventional design and are simplified in FIGS. 1A, 1B, and 1C. As shown in FIGS. 1A, 1B, and 1C, heat may be supplied to the base of each column or to a circulating bottom stream through a heat exchanger or reboiler. Other types of reboilers, such as internal reboilers, may also be used in some embodiments. The heat that is provided to reboilers may be derived from any heat generated during the process that is integrated with the reboilers or from an external source such as another heat generating chemical process or a boiler. Although one reactor and one flasher are shown in FIGS. 1A, 1B, and 1C, additional reactors, flashers, condensers, heating elements, and other components may be used in embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in any of the columns may vary. As a practical matter, pressures from 10 KPa to 3000 KPa will generally be employed in these zones although in some embodiments subatmospheric pressures may be employed as well as superatmospheric pressures. Temperatures within the various zones will normally range between the boiling points of the composition removed as the distillate and the composition removed as the residue. It will be recognized by those skilled in the art that the temperature at a given location in an operating distillation column is dependant on the composition of the material at that location and the pressure of column. In addition, feed rates may vary depending on the size of the production process and, if described, may be generically referred to in terms of feed weight ratios.

When column 107 is operated under standard atmospheric pressure, the temperature of the residue exiting in line 116 from column 107 preferably is from 95° C. to 120° C., e.g., from 105° C. to 117° C. or from 110° C. to 115° C. The temperature of the distillate exiting in line 117 from column 107 preferably is from 70° C. to 110° C., e.g., from 75° C. to 95° C. or from 80° C. to 90° C. In other embodiments, the pressure of first column 107 may range from 0.1 KPa to 510 KPa, e.g., from 1 KPa to 475 KPa or from 1 KPa to 375 KPa. Exemplary components of the distillate and residue compositions for first column 107 are provided in Table 3 below. It should also be understood that the distillate and residue may also contain other components, not listed, such as components in the feed. For convenience, the distillate and residue of the first column may also be referred to as the "first distillate" or "first residue." The distillates or residues of the other columns may also be referred to with similar numeric modifiers (second, third, etc.) in order to distinguish them from one another, but such modifiers should not be construed as requiring any particular separation order.

TABLE 3

FIRST COLUMN

|  | Conc. (wt. %) | Conc. (wt. %) | Conc. (wt. %) |
|---|---|---|---|
| Distillate |  |  |  |
| Ethanol | 20 to 75 | 30 to 70 | 40 to 65 |
| Higher Alcohol* | 0.01 to 20 | 0.04 to 20 | 0.5 to 10 |
| Water | 10 to 40 | 15 to 35 | 20 to 35 |
| Acetic Acid | <2 | 0.001 to 0.5 | 0.01 to 0.2 |
| Ethyl Acetate | <60 | 5.0 to 40 | 10 to 30 |
| Acetaldehyde | <10 | 0.001 to 5 | 0.01 to 4 |
| Diethyl Ether | 0.02 to 7.5 | 0.3 to 6.5 | 1.2 to 5 |
| Acetal | <0.1 | <0.1 | <0.05 |
| Acetone | <0.05 | 0.001 to 0.03 | 0.01 to 0.025 |

TABLE 3-continued

FIRST COLUMN

|  | Conc. (wt. %) | Conc. (wt. %) | Conc. (wt. %) |
|---|---|---|---|
| Residue |  |  |  |
| Acetic Acid | 60 to 100 | 70 to 95 | 85 to 92 |
| Higher Acid** | 0.01 to 20 | 0.04 to 20 | 0.5 to 10 |
| Water | <30 | 1 to 20 | 1 to 15 |
| Ethanol | <1 | <0.9 | <0.07 |

As shown in Table 3, without being bound by theory, it has surprisingly and unexpectedly been discovered that when any amount of acetal is detected in the feed that is introduced to the acid separation column (first column 107), the acetal appears to decompose in the column such that less or even no detectable amounts are present in the distillate and/or residue.

Depending on the reaction conditions, the crude alcohol product exiting reactor 103 in line 112 may comprise ethanol, higher alcohol, acetic acid (unconverted), higher acid (unconverted), ethyl acetate, and water. After exiting reactor 103, a non-catalyzed equilibrium reaction may occur between the components contained in the crude alcohol product until it is added to flasher 106 and/or first column 107. This equilibrium reaction tends to drive the crude alcohol product to an equilibrium between ethanol/acetic acid and ethyl acetate/water, as shown below. Similar equilibria exist for the higher acids and higher alcohols.

In the event the crude alcohol product is temporarily stored, e.g., in a holding tank, prior to being directed to distillation zone 102, extended residence times may be encountered. Generally, the longer the residence time between reaction zone 101 and distillation zone 102, the greater the formation of ethyl acetate. For example, when the residence time between reaction zone 101 and distillation zone 102 is greater than 5 days, significantly more ethyl acetate may form at the expense of ethanol. Thus, shorter residence times between reaction zone 101 and distillation zone 102 are generally preferred in order to maximize the amount of ethanol formed. In one embodiment, a holding tank (not shown), is included between the reaction zone 101 and distillation zone 102 for temporarily storing the liquid component from line 115 for up to 5 days, e.g., up to 1 day, or up to 1 hour. In a preferred embodiment no tank is included and the condensed liquids are fed directly to the first distillation column 107. In addition, the rate at which the non-catalyzed reaction occurs may increase as the temperature of the crude alcohol product, e.g., in line 115, increases. These reaction rates may be particularly problematic at temperatures exceeding 30° C., e.g., exceeding 40° C. or exceeding 50° C. Thus, in one embodiment, the temperature of liquid components in line 115 or in the optional holding tank is maintained at a temperature less than 40° C., e.g., less than 30° C. or less than 20° C. One or more cooling devices may be used to reduce the temperature of the liquid in line 115.

As discussed above, a holding tank (not shown) may be included between the reaction zone 101 and distillation zone 102 for temporarily storing the liquid component from line 115, for example from 1 to 24 hours, optionally at a temperature of about 21° C., and corresponding to an ethyl acetate formation of from 0.01 wt. % to 1.0 wt. % respectively. In addition, the rate at which the non-catalyzed reaction occurs may increase as the temperature of the crude alcohol product is increased. For example, as the temperature of the crude alcohol product in line 115 increases from 4° C. to 21° C., the rate of ethyl acetate formation may increase from about 0.01 wt. % per hour to about 0.005 wt. % per hour. Thus, in one embodiment, the temperature of liquid components in line 115 or in the optional holding tank is maintained at a temperature less than 21° C., e.g., less than 4° C. or less than −10° C.

In addition, it has now been discovered that the above-described equilibrium reaction may also favor ethanol formation in the top region of first column 107.

The distillate, e.g., overhead stream, of first column 107 optionally is condensed and refluxed as shown in FIGS. 1A-C, preferably, at a reflux ratio of 1:5 to 10:1. The distillate in line 117 preferably comprises ethanol and one or more higher alcohols, which may serve as an in situ denaturant, as well as ethyl acetate, acetaldehyde, water, and other impurities, which may be difficult to separate due to the formation of binary and tertiary azeotropes. The first distillate also comprises a significantly reduced amount of acetic acid and higher acid. As shown in FIG. 1C, in some embodiments, the distillate of the first column (without further processing) is a denatured ethanol composition comprising from 0.0001 wt. % to 80 wt. % denaturant, e.g., from 0.001 wt. % to 60 wt. %, and from 20 wt. % to 75 wt. % ethanol, e.g., from 30 wt. % to 70 wt. %. Preferably, the denaturant in these embodiments is the higher alcohol optionally in combination with ethyl acetate and/or acetaldehyde.

In another embodiment, at least a portion of the first distillate may be combined, via optional line 117', with a purified ethanol stream to form a denatured ethanol composition. Preferably, the denaturant comprises the higher alcohol optionally in combination with ethyl acetate and/or acetaldehyde. In another embodiment, at least a portion of the first distillate may be fed to an additional column, e.g., a third column as discussed below. As a result, the denaturant(s) in the first distillate, e.g., the higher alcohol, ethyl acetate and/or acetaldehyde, may be carried through to the distillate of the third column. As such, the third distillate may be denatured ethanol composition comprising the denaturant(s) from the first distillate. In these embodiments, the weight percentages of the denaturant(s) in the denatured ethanol composition may be as previously discussed. The weight ratio of the denaturant-containing stream, e.g., line 117, and the purified ethanol stream vary widely and may be adjusted so as to achieve a particular desired concentration of denaturant in the denatured ethanol composition. For example, the weight ratio of the purified ethanol stream to the denaturant-containing stream may range from 0.01:1 to 5:1, e.g., from 0.05:1 to 3:1.

As discussed above, the residue from first column 107 comprises an amount of unreacted acetic acid and unreacted higher acid. Thus, in another embodiment, at least a portion of the first residue may be combined with a purified ethanol stream to form an acetic acid-denatured ethanol composition.

Beneficially, these denatured ethanol compositions are produced utilizing denaturant that is formed in situ via the hydrogenation reaction and without additional separation steps. As such, it is not necessary to provide an additional outside source of denaturant or to combine denaturant and purified ethanol, which eliminates a process step, and simplifies the overall process. It is also within the scope of the invention to further purify the first column distillate to remove, for example, additional water and/or acetaldehyde. Conventional separation methods may be used to achieve this additional purification.

As shown in Table 3, the first residue comprises a significant portion of unreacted acetic acid and heavier acid, which may, in turn, be recycled back to reactor 103, as shown in FIGS. 1A, 1B, and 1C.

The first distillate in line 117 is introduced to the second column 108, also referred to as the "light ends column," preferably in the middle part of column 108, e.g., middle half or middle third. Second column 108 may be a tray column or packed column. In one embodiment, second column 108 is a tray column having from 5 to 70 trays, e.g., from 15 to 50 trays or from 20 to 45 trays.

As one example, when a 25 tray column is utilized in a column without water extraction, line 117 is introduced at tray 17. When the second column is not an extractive distillation column, it is expected that the ethyl acetate in line 117 may be separated into the second residue along with the ethanol, the higher alcohol and water. As a result, in one embodiment, more ethyl acetate may be fed to third column 109 and, thus, this ethyl acetate may be present in the third distillate. In other embodiments, at least a portion of the ethyl acetate-containing second residue may be combined with a purified ethanol stream to form a denatured ethanol composition comprising ethanol, the higher alcohol and ethyl acetate.

In preferred embodiments, however, the second column 108 may be an extractive distillation column. In extractive distillation columns, it is expected that the ethyl acetate in line 117 may be separated from the ethanol, the higher alcohol and water and pass into the second distillate. In such embodiments, an extraction agent, such as water, may be optionally added to second column 108 via line 127. If the extraction agent comprises water, it may be obtained from an external source or from an internal return/recycle line from one or more of the other columns. In a preferred embodiment, the water in the third residue of third column 109 is utilized as the extraction agent. As shown in FIGS. 1A, 1B, and 1C, the third residue may be optionally directed to second column 108 via line 121'.

Although the temperature and pressure of second column 108 may vary, when at atmospheric pressure the temperature of the second residue exiting in line 118 from second column 108 preferably is from 60° C. to 90° C., e.g., from 70° C. to 90° C. or from 80° C. to 90° C. The temperature of the second distillate exiting in line 120 from second column 108 preferably is from 50° C. to 90° C., e.g., from 60° C. to 80° C. or from 60° C. to 70° C. Column 108 may operate at atmospheric pressure. In other embodiments, the pressure of second column 108 may range from 0.1 KPa to 510 KPa, e.g., from 1 KPa to 475 KPa or from 1 KPa to 375 KPa. Exemplary components for the distillate and residue compositions for second column 108 are provided in Table 4 below. It should be understood that the distillate and residue may also contain other components, not listed, such as components in the feed.

TABLE 4

| SECOND COLUMN | | | |
|---|---|---|---|
| | Conc. (wt. %) | Conc. (wt. %) | Conc. (wt. %) |
| Distillate | | | |
| Ethyl Acetate | 10 to 90 | 25 to 90 | 50 to 90 |
| Acetaldehyde | 1 to 25 | 1 to 15 | 1 to 8 |
| Water | 1 to 25 | 1 to 20 | 4 to 16 |
| Ethanol | <30 | 0.001 to 15 | 0.01 to 5 |
| Higher Alcohol* | <20 | <10 | <2 |
| Acetal | <5 | 0.001 to 2 | 0.01 to 1 |
| Residue | | | |
| Water | 30 to 70 | 30 to 60 | 30 to 50 |
| Ethanol | 20 to 75 | 30 to 70 | 40 to 70 |
| Higher Alcohol* | 0.01 to 20 | 0.04 to 20 | 0.5 to 10 |

TABLE 4-continued

| SECOND COLUMN | | | |
|---|---|---|---|
| | Conc. (wt. %) | Conc. (wt. %) | Conc. (wt. %) |
| Ethyl Acetate | <3 | 0.001 to 2 | 0.001 to 0.5 |
| Acetic Acid | <0.5 | 0.001 to 0.3 | 0.001 to 0.2 |
| Higher Acid** | <0.5 | 0.001 to 0.3 | 0.001 to 0.2 |

The weight ratio of alcohols (ethanol and higher alcohols) in the second residue to alcohols in the second distillate preferably is at least 3:1, e.g., at least 6:1, at least 8:1, at least 10:1 or at least 15:1. The weight ratio of ethyl acetate in the second residue to ethyl acetate in the second distillate preferably is less than 0.4:1, e.g., less than 0.2:1 or less than 0.1:1. In embodiments that use an extractive column with water as an extraction agent as the second column 108, the weight ratio of ethyl acetate in the second residue to ethyl acetate in the second distillate approaches zero. Thus, as shown in Table 4, the second distillate in line 120, which is a derivative stream of the crude alcohol product, comprises a significant amount of separated, in situ, denaturant and the second residue in line 118 comprises a significant amount of alcohols (ethanol and higher alcohols). In some embodiments, the second distillate comprises diethyl ether. The diethyl ether may be present in amounts ranging from 0.1 wt. % to 20 wt. %, e.g., 0.1 wt. % to 10 wt. %, from 1 wt. % to 9 wt. %, or from 3 wt. % to 7 wt. %. In these cases, the second distillate may be a denatured ethanol composition having a denaturant comprising the higher alcohol and diethyl ether. In one embodiment, the second residue in line 118 further comprises isopropanol. The isopropanol may be derived from acetone via the methods discussed above. The acetone, for example, may be formed in situ in the hydrogenation and/or the acetone may be added to the hydrogenation reactor as a reactant. Thus, in embodiments where a sufficient amount of isopropanol, e.g., from 0.1 wt. % to 10 wt. %, from 1 wt. % to 9 wt. %, or from 3 wt. % to 7 wt. %, is present in the second residue, the second residue may be a denatured ethanol composition having an isopropanol denaturant.

In another embodiment of the invention as shown in FIG. 1A, at least a portion of the second distillate is directed, e.g., via line 120, to the purified mixed alcohol composition exiting third column 109. In this case, the denatured ethanol composition results from the addition of the in situ-formed non-alcohol denaturant to the purified mixed alcohol composition. Preferably, ethyl acetate denaturant in the second distillate is combined with the purified mixed alcohol composition obtained from third column 109. In other embodiments, acetaldehyde denaturant in the second distillate is combined with the purified mixed alcohol composition obtained from third column 109. In other embodiments, at least a portion of the second distillate is fed to third column 109. In these cases, at least a portion of the denaturant in the second distillate, e.g., ethyl acetate and/or acetaldehyde, follows the ethanol through third column 109 along with the higher alcohol. Other impurities in the second distillate may be withdrawn in the residue of the third column 109. As a result, the third distillate comprises ethanol and the higher alcohol along with denaturant from the second column distillate. Denatured ethanol compositions thus formed may have the characteristics and composition of the denatured ethanol compositions discussed herein. The weight ratio of the denaturant-containing stream, e.g., line 120, and the purified mixed alcohol stream vary widely and may be adjusted so as to achieve a particular desired concentration of ethanol and higher alcohol as well as additional denaturant. For example, when ethyl acetate is the additional denaturant, the weight ratio of the purified mixed alcohol stream to the denaturant-containing stream may range from 100:1 to 1:1, e.g., from 25:1 to 5:1.

In another embodiment, at least a portion of the second distillate is recycled to reactor 103 (not shown). As shown, the second residue from the bottom of second column 108, which comprises ethanol, higher alcohol and water, is fed via line 118 to third column 109, also referred to as the "product column." More preferably, the second residue in line 118 is introduced in the lower part of third column 109, e.g., lower half or lower third. Third column 109 recovers ethanol and the higher alcohols, which preferably is substantially pure mixed alcohol composition other than the azeotropic water content, as the distillate in line 119. Particularly heavy alcohols may be separated into the third residue 121. The distillate of third column 109 preferably is refluxed as shown in FIG. 1A, for example, at a reflux ratio of from 1:10 to 10:1, e.g., from 1:3 to 3:1 or from 1:2 to 2:1. The third residue in line 121, which preferably comprises primarily water, preferably is removed from the system 100 or may be partially returned to any portion of the system 100. Third column 109 is preferably a tray column as described above and preferably operates at atmospheric pressure. The temperature of the third distillate exiting in line 119 from third column 109 preferably is from 60° C. to 110° C., e.g., from 70° C. to 100° C. or from 75° C. to 95° C. The temperature of the third residue exiting from third column 109 preferably is from 70° C. to 115° C., e.g., from 80° C. to 110° C. or from 85° C. to 105° C., when the column is operated at atmospheric pressure. Exemplary components of the distillate, residue, and optional side stream compositions for third column 109 are provided in Table 5 below. As shown in Table 5, the third distillate may comprise significant amounts of higher alcohol denaturant, preferably propanol denaturant. In these cases, the third distillate may be a denatured ethanol composition. It should be understood that the distillate and residue may also contain other components, not listed, such as components from the feed.

As separation occurs in the third column, the composition of the stream being separated may vary from tray to tray in the third column. In some embodiments, the composition of the stream within the third column, depending upon operating conditions, may contain an increased concentration or build up of higher alcohols, e.g., mid-boiling alcohols having a boiling point lower than that of water and higher than that of an ethanol/water low-boiling azeotrope. Examples of these higher alcohols include n-propanol (boiling point 97.1° C.), isopropanol (boiling point 82.5° C.), and 2-butanol (boiling point 99.5° C.). Some of these alcohols are formed in situ as a result of the acetic acid hydrogenation and/or from the hydrogenation of the higher acids. These in situ-formed higher alcohols may be utilized as denaturants.

The mid-boiling point higher alcohols may be removed using one or more side streams 138 drawn from third column 109. Preferably, side stream 138 is drawn from a middle or an upper section of third column 109, above the feed point of the second residue. Most preferably, side stream 138 is drawn from above the tray 25, e.g., from above tray 30, or from above tray 40. By adjusting the process parameters of third column 109 and withdrawing side stream 138 at the appropriate location, side stream 138 may be used to remove a significant portion of mid-boiling point alcohols, e.g., n-propanol, as desired, from the feed in line 118. Side stream 138 may comprise, for example, from 0.01 wt. % to 10 wt. % n-propanol, e.g., from 0.01 to 5 wt. % or from 0.01 wt. % to 3 wt. %. By withdrawing side stream 138, a significant amount of propanol, e.g., n-propanol, may be removed resulting in the purification of the ethanol in the third distillate in line 119, if desired. It is within the scope of the invention to select, based on column configuration and operating conditions, an appropriate tray in a column from which to draw a particular side stream. Also, the contents of side stream 138 may constitute a denatured ethanol composition comprising ethanol and mid-boiling heavier alcohols such as propanol, e.g., n-propanol. Thus, in this embodiment, a pure ethanol composition may be co-produced with a denatured ethanol composition. In other embodiments, side stream 138 and the third distillate are each, independently of one another, denatured ethanol compositions. For example, side stream 130 may comprise a heavier alcohol-denatured ethanol composition, e.g., an n-propanol-denatured ethanol composition, and third distillate 119 may comprise an ethyl acetate-denatured ethanol composition. By performing the separation in this manner, the resultant third distillate 119 comprises less heavier alcohol than the side stream, which may be desired for certain ethanol applications. In other embodiments, at least a portion of withdrawn side stream 138 may be combined with third distillate 119 to form a denatured ethanol composition comprising at least a portion of the in situ-formed denaturant from side stream 130.

TABLE 5

THIRD COLUMN

|  | Conc. (wt. %) | Conc. (wt. %) | Conc. (wt. %) |
|---|---|---|---|
| Distillate |  |  |  |
| Ethanol | 75 to 96 | 80 to 96 | 85 to 96 |
| Heavier Alcohol* | 0.01 to 20 | 0.04 to 20 | 0.5 to 10 |
| Water | <12 | 1 to 9 | 3 to 8 |
| Acetic Acid | <1 | 0.001 to 0.1 | 0.005 to 0.01 |
| Ethyl Acetate | <5 | 0.001 to 4 | 0.01 to 3 |
| Isopropanol | 0.07 to 10 | 0.8 to 7 | 2.5 to 7 |
| Residue |  |  |  |
| Water | 75 to 100 | 80 to 100 | 90 to 100 |
| Ethanol | <0.8 | 0.001 to 0.5 | 0.005 to 0.05 |
| Heavier Alcohol* | <0.8 | 0.001 to 0.5 | 0.005 to 0.05 |
| Ethyl Acetate | <1 | 0.001 to 0.5 | 0.005 to 0.2 |
| Acetic Acid | <2 | 0.001 to 0.5 | 0.005 to 0.2 |
| Side Stream (Optional) |  |  |  |
| Ethanol | 0.01 to 10 | 0.01 to 5 | 0.01 to 3 |
| n-propanol | 0.1 to 10 | 0.25 to 8 | 1.5 to 6.3 |

Concentrations of the heavier alcohols will vary widely depending on the boiling point of the various heavier alcohols as well as whether a side stream is employed.

Any of the compounds that are carried through the distillation process from the feed or crude reaction product generally remain in the third distillate in amounts of less 0.1 wt. %, based on the total weight of the third distillate composition, e.g., less than 0.05 wt. % or less than 0.02 wt. %. In one embodiment, one or more side streams may remove impurities from any of the columns 107, 108, and/or 109 in system 100. In one embodiment, at least one side stream may be used to remove impurities from the third column 109. The impurities may be purged and/or retained within the system 100.

The third distillate in line 119 may be further purified to form an anhydrous mixed alcohol product stream, i.e., "finished anhydrous alcohol," using one or more additional separation systems, such as, for example, distillation columns (e.g., a finishing column) or molecular sieves.

Returning to second column 108, the distillate in line 120 preferably is refluxed as shown in FIGS. 1A, 1B, and 1C, for example, at a reflux ratio of from 1:10 to 10:1, e.g., from 1:5 to 5:1 or from 1:3 to 3:1. As noted above, the second distillate may comprise a significant portion denaturants, e.g., ethyl acetate and/or acetaldehyde. Accordingly, all or a portion of the second distillate, as shown by line 120, may be directed downstream and may be combined with the mixed alcohols that have been further purified, e.g., via third column 109. Also, at least a portion of the distillate from second column 108 may be purged if necessary. In another embodiment, as shown in FIG. 1B, a portion of the second distillate from second column 108 may be recycled to reaction zone 101 via line 120 in order to convert ethyl acetate to additional ethanol, e.g., may be recycled to reactor 103 and co-fed along with acid feed line 105. In another embodiment, the second distillate in line 120 may be further purified to remove other components, such as acetaldehyde, using one or more additional columns (not shown). Such a configuration may be utilized in a case where the desired denaturant consists essentially of ethyl acetate, e.g., Formulae 35 or 35-A of Title 27, Part 21 of the US Code of Federal Regulations (hereinafter abbreviated as 27 C.F.R. Part 21), the entirety of which is incorporated herein by reference. As another option, additional columns (not shown) may be utilized to remove the ethyl acetate and leave acetaldehyde, which may be useful in a situation where the desired denaturant comprises acetaldehyde and does not comprise ethyl acetate.

System 100 in FIG. 1C is similar to that of FIGS. 1A and 1B, with the addition that the second distillate in line 120 is fed to fourth column 123, also referred to as the "acetaldehyde removal column." In fourth column 123, the second distillate is separated into a fourth distillate, which comprises acetaldehyde in line 124 and a fourth residue, which comprises ethyl acetate in line 125. The fourth distillate preferably is refluxed at a reflux ratio of from 1:20 to 20:1, e.g., from 1:10 to 10:1 or from 1:5 to 5:1, and at least a portion of the fourth distillate may be returned to the reaction zone 101 as shown by line 124. For example, the fourth distillate may be combined with the acid feed, added to the vaporizer 110, or added directly to the reactor 103. As shown, the fourth distillate is co-fed with the acetic acid in feed line 105 to vaporizer 110. Without being bound by theory, since acetaldehyde may be hydrogenated to form ethanol, the recycling of a stream that contains acetaldehyde to the reaction zone increases the yield of ethanol and decreases byproduct and waste generation. In another embodiment (not shown in the figure), the acetaldehyde may be collected and utilized, with or without further purification, to make useful products including but not limited to n-butanol, 1,3-butanediol, and/or crotonaldehyde and derivatives. In one preferred embodiment, the acetaldehyde is removed from the second distillate in fourth column 123 such that no detectable amount of acetaldehyde is present in the residue of column 123.

In preferred embodiments, at least a portion of fourth distillate is combined (not shown) with the purified mixed alcohol stream comprising the ethanol and heavier alcohol to form a denatured ethanol composition. Preferably, the denaturant comprises the heavier alcohol as well as acetaldehyde and/or ethyl acetate. In other embodiments, at least a portion of the fourth distillate may be fed to third column 109. As a result, in these embodiments, the distillate exiting third column 109 may comprise at least a portion of the in situ-formed acetaldehyde and/or ethyl acetate that was present in the fourth distillate. In these embodiments, the weight percentages of the acetaldehyde denaturant in the denatured ethanol composition may be as previously discussed. The weight ratio of the purified mixed alcohol stream and the fourth distillate may vary widely and may be adjusted so as to achieve a particular desired concentration of non-alcohol denaturant in the denatured ethanol composition. For example, the weight ratio of the purified mixed alcohol stream to the fourth distillate may range from 2:1 to 75:1, e.g., from 7:1 to 50:1.

The fourth residue primarily comprises ethyl acetate and ethanol. Preferably, at least a portion of fourth residue is combined with the purified mixed alcohol stream to form a denatured ethanol composition. Preferably, the denaturant comprises ethyl acetate as well as the heavier alcohol. In other embodiments, at least a portion of the fourth residue may be fed to third column 109. As a result, in these embodiments, the distillate exiting third column 109 may comprise at least a portion of the in situ-formed ethyl acetate that was present in the fourth residue. In these embodiments, the weight percentages of the ethyl acetate denaturant in the denatured ethanol composition may be as previously discussed. The weight ratio of the purified mixed alcohol stream and the fourth residue may vary widely and may be adjusted so as to achieve a particular desired concentration of denaturant in the denatured ethanol composition. For example, the weight ratio of the purified mixed alcohol stream to the fourth residue may range from 1:1 to 50:1, e.g., from 1.75:1 to 20:1. The fourth residue of fourth column 123, in other embodiments, may be purged via line 125.

Fourth column 123 is preferably a tray column as described above and preferably operates above atmospheric pressure. In one embodiment, the pressure is from 120 KPa to 5,000 KPa, e.g., from 200 KPa to 4,500 KPa, or from 400 KPa to 3,000 KPa. In a preferred embodiment the fourth column 123 may operate at a pressure that is higher than the pressure of the other columns.

The temperature of the fourth distillate exiting in line 124 from fourth column 123 preferably is from 60° C. to 110° C., e.g., from 70° C. to 100° C. or from 75° C. to 95° C. The temperature of the residue exiting from fourth column 125 preferably is from 70° C. to 115° C., e.g., from 80° C. to 110° C. or from 85° C. to 110° C. Exemplary components of the distillate and residue compositions for fourth column 123 are provided in Table 6 below. It should be understood that the distillate and residue may also contain other components, not listed, such as components in the feed.

TABLE 6

FOURTH COLUMN

| | Conc. (wt. %) | Conc. (wt. %) | Conc. (wt. %) |
|---|---|---|---|
| Distillate | | | |
| Acetaldehyde | 2 to 80 | 2 to 50 | 5 to 40 |
| Ethyl Acetate | <90 | 30 to 80 | 40 to 75 |
| Ethanol | <30 | 0.001 to 25 | 0.01 to 20 |
| Heavier Alcohol* | <30 | 0.001 to 25 | 0.01 to 20 |
| Water | <25 | 0.001 to 20 | 0.01 to 15 |
| Residue | | | |
| Ethyl Acetate | 40 to 100 | 50 to 100 | 60 to 100 |
| Ethanol | <40 | 0.001 to 30 | 0.01 to 15 |
| Heavier Alcohol* | <40 | 0.001 to 30 | 0.01 to 15 |
| Water | <25 | 0.001 to 20 | 2 to 15 |
| Acetaldehyde | <1 | 0.001 to 0.5 | Not detectable |
| Acetal | <3 | 0.001 to 2 | 0.01 to 1 |

FIG. 1C also shows that the third residue in line 121 may be recycled to second column 108. In one embodiment, recycling the third residue further reduces the aldehyde components in the second residue and concentrates these aldehyde components in the distillate stream 120 and thereby sent to the fourth column 123, wherein the aldehydes may be more easily separated in the fourth column 123. Such embodiments also provide a finished ethanol product that preferably has low amounts of aldehydes and esters.

In several embodiments, denaturant-containing streams are combined with purified mixed alcohol streams to form denatured ethanol compositions. In other embodiments, these denaturant-containing streams may be fed to third column 109, as opposed to being combined with the distillate of third column 109. In these cases, the denaturants that are fed to column 109 may be separated in the distillate of the third column 109 and, as such may be present in the purified mixed alcohol stream. Thus, the third distillate may comprise a denatured ethanol composition.

Alternative two-column separation schemes are illustrated in FIGS. 2 and 3. In FIG. 2, crude alcohol product in line 115 is introduced in the middle or lower portion of a first column 150, also referred to as acid-water column. For purposes of convenience, the columns in each exemplary separation process, may be referred as the first, second, third, etc., columns, but it is understood that first column 150 in FIG. 2 operates differently than the first column 107 of FIGS. 1A-1C. In one embodiment, no entrainers are added to first column 150. In FIG. 2, first column 150, water and unreacted acetic acid and unreacted heavier acid, along with any other heavy components, if present, are removed from stream 115 and are withdrawn, preferably continuously, as a first residue in line 151. Preferably, a substantial portion of the water in the crude alcohol product that is fed to first column 150 may be removed in the first residue, for example, up to about 90% of the water from the crude ethanol product, and more preferably up to about 75%. First column 150 also forms a first distillate, which is withdrawn in line 152.

When column 150 is operated under about 170 kPa, the temperature of the residue exiting in line 151 preferably is from 90° C. to 130° C., e.g., from 95° C. to 120° C. or from 100° C. to 115° C. The temperature of the distillate exiting in line 152 preferably is from 60° C. to 90° C., e.g., from 65° C. to 85° C. or from 70° C. to 80° C. In some embodiments, the pressure of first column 150 may range from 0.1 kPa to 510 kPa, e.g., from 1 kPa to 475 kPa or from 1 kPa to 375 kPa.

The first distillate in line 152 comprises water, in addition to ethanol, the higher alcohol and other organics. In terms of ranges, the concentration of water in the first distillate in line 152 preferably is from 4 wt. % to 38 wt. %, e.g., from 7 wt. % to 32 wt. %, or from 7 to 25 wt. %. A portion of first distillate in line 153 may be condensed and refluxed, for example, at a ratio of from 10:1 to 1:10, e.g., from 3:1 to 1:3 or from 1:2 to 2:1. It is understood that reflux ratios may vary with the number of stages, feed locations, column efficiency and/or feed composition. Operating with a reflux ratio of greater than 3:1 may be less preferred because more energy may be required to operate the first column 150. The condensed portion of the first distillate may also be fed to a second column 154.

The remaining portion of the first distillate in 155 is fed to a water separation unit 156. Water separation unit 156 may be an adsorption unit, membrane, molecular sieves, extractive column distillation, or a combination thereof. A membrane or an array of membranes may also be employed to separate water from the distillate. The membrane or array of membranes may be selected from any suitable membrane that is capable of removing a permeate water stream from a stream that also comprises ethanol and ethyl acetate.

In a preferred embodiment, water separation unit 156 is a pressure swing adsorption (PSA) unit. The PSA unit is optionally operated at a temperature from 30° C. to 160° C., e.g., from 80° C. to 140° C., and a pressure of from 0.01 kPa to 550 kPa, e.g., from 1 kPa to 150 kPa. The PSA unit may comprise two to five beds. Water separation unit 156 may remove at least 95% of the water from the portion of first distillate in line 155, and more preferably from 99% to 99.99% of the water from the first distillate, in a water stream 157. All or a portion of water stream 157 may be returned to column 150 in line 158, where the water preferably is ultimately recovered from column 150 in the first residue in line 151. Additionally or alternatively, all or a portion of water stream 157 may be purged via line 159. The remaining portion of first distillate exits the water separation unit 156 as mixed alcohol stream 160. Mixed alcohol stream 160 may have a low concentration of water of less than 10 wt. %, e.g., less than 6 wt. % or less than 2 wt. %. Exemplary components of mixed alcohol stream 160 and first residue in line 151 are provided in Table 7 below. It should also be understood that these streams may also contain other components, not listed, such as components derived from the feed.

TABLE 7

FIRST COLUMN 150 WITH PSA (FIG. 2)

|  | Conc. (wt. %) | Conc. (wt. %) | Conc. (wt. %) |
|---|---|---|---|
| Mixed Alcohol Stream |  |  |  |
| Ethanol | 20 to 95 | 30 to 95 | 40 to 95 |
| Higher Alcohol* | 0.01 to 20 | 0.04 to 20 | 2 to 8 |
| Water | <10 | 0.01 to 6 | 0.1 to 2 |
| Acetic Acid | <2 | 0.001 to 0.5 | 0.01 to 0.2 |
| Higher Acid** | <2 | 0.001 to 0.5 | 0.01 to 0.2 |
| Ethyl Acetate | <60 | 1 to 55 | 5 to 55 |
| Acetaldehyde | <1 | 0.001 to 0.5 | 0.005 to 0.05 |
| Acetal | <0.1 | <0.05 | <0.01 |
| Acetone | <0.05 | 0.001 to 0.03 | 0.01 to 0.025 |
| Residue |  |  |  |
| Acetic Acid | <90 | 1 to 50 | 2 to 35 |
| Higher Acid** | 0.1 to 40 | 1 to 20 | 1 to 10 |
| Water | 30 to 100 | 45 to 95 | 60 to 90 |
| Ethanol | <1 | <0.9 | <0.3 |
| Higher Alcohol* | <1 | <0.9 | <0.3 |

Preferably, mixed alcohol stream 160 is not returned or refluxed to first column 150. The condensed portion of the first distillate in line 153 may be combined with mixed alcohol stream 160 to control the amount of water fed to the second column 154. For example, in some embodiments the first distillate may be split into equal portions, while in other embodiments, all of the first distillate may be condensed or all of the first distillate may be processed in the water separation unit. In FIG. 2, the condensed portion in line 153 and mixed alcohol stream 160 are co-fed to second column 154. In other embodiments, the condensed portion in line 153 and mixed alcohol stream 160 may be separately fed to second column 154. The combined distillate and mixed alcohol stream preferably has a total water concentration of greater than 0.5 wt. %, e.g., greater than 2 wt. % or greater than 5 wt. %. In terms of ranges, the total water concentration of the combined distillate and mixed alcohol stream may be from 0.5 to 15 wt. %, e.g., from 2 to 12 wt. %, or from 5 to 10 wt. %.

The second column 154 in FIG. 2, also referred to as the "light ends column," removes ethyl acetate and acetaldehyde from the first distillate in line 153 and/or mixed alcohol stream 160. Ethyl acetate and acetaldehyde are removed as a second distillate in line 161 and ethanol and the higher alcohol are removed as the second residue in line 162. Second column 154 may be a tray column or packed column. In one embodiment, second column 154 is a tray column having from 5 to 70 trays, e.g., from 15 to 50 trays or from 20 to 45 trays.

Second column 154 operates at a pressure ranging from 0.1 kPa to 510 kPa, e.g., from 10 kPa to 450 kPa or from 50 kPa to 350 kPa. Although the temperature of second column 154 may vary, when at about 20 kPa to 70 kPa, the temperature of the second residue exiting in line 162 preferably is from 30° C. to 75° C., e.g., from 35° C. to 70° C. or from 40° C. to 65° C. The temperature of the second distillate exiting in line 161 preferably is from 20° C. to 55° C., e.g., from 25° C. to 50° C. or from 30° C. to 45° C.

The total concentration of water fed to second column 154 preferably is less than 10 wt. %, as discussed above. When first distillate in line 153 and/or mixed alcohol stream 160 comprises minor amounts of water, e.g., less than 1 wt. % or less than 0.5 wt. %, additional water may be fed to the second column 154 as an extractive agent in the upper portion of the column. A sufficient amount of water is preferably added via the extractive agent such that the total concentration of water fed to second column 154 is from 1 to 10 wt. % water, e.g., from 2 to 6 wt. %, based on the total weight of all components fed to second column 154. If the extractive agent comprises water, the water may be obtained from an external source or from an internal return/recycle line from one or more of the other columns or water separators.

Suitable extractive agents may also include, for example, dimethylsulfoxide, glycerine, diethylene glycol, 1-naphthol, hydroquinone, N,N'-dimethylformamide, 1,4-butanediol; ethylene glycol-1,5-pentanediol; propylene glycol-tetraethylene glycol-polyethylene glycol; glycerine-propylene glycol-tetraethylene glycol-1,4-butanediol, ethyl ether, methyl formate, cyclohexane, N,N'-dimethyl-1,3-propanediamine, N,N'-dimethylethylenediamine, diethylene triamine, hexamethylene diamine and 1,3-diaminopentane, an alkylated thiopene, dodecane, tridecane, tetradecane, chlorinated paraffins, or a combination thereof. When extractive agents are used, a suitable recovery system, such as a further distillation column, may be used to recycle the extractive agent.

Exemplary components for the second distillate and second residue compositions for the second column 154 are provided in Table 8, below. It should be understood that the distillate and residue may also contain other components, not listed in Table 8.

TABLE 8

SECOND COLUMN 154 (FIG. 2)

|  | Conc. (wt. %) | Conc. (wt. %) | Conc. (wt. %) |
|---|---|---|---|
| Second Distillate | | | |
| Ethyl Acetate | 5 to 90 | 10 to 80 | 15 to 75 |
| Acetaldehyde | <10 | 0.005 to 2 | 0.01 to 1 |
| Ethanol | <45 | 0.001 to 40 | 0.01 to 35 |
| Higher Alcohol* | <45 | 0.001 to 40 | 0.01 to 35 |
| Water | <20 | 0.01 to 10 | 0.1 to 5 |
| Second Residue | | | |
| Ethanol | 80 to 99.5 | 85 to 99.5 | 90 to 99.5 |
| Heavier Alcohol* | 0.01 to 20 | 0.04 to 20 | 0.5 to 10 |
| Water | <20 | 0.001 to 15 | 0.01 to 10 |
| Ethyl Acetate | <1 | 0.001 to 2 | 0.001 to 0.5 |
| Acetic Acid | <0.5 | <0.01 | 0.001 to 0.01 |
| Heavier Acid** | <0.5 | <0.01 | 0.001 to 0.01 |

The second distillate in line 161, which comprises ethyl acetate and/or acetaldehyde, preferably is refluxed as shown in FIG. 2, for example, at a reflux ratio of from 1:30 to 30:1, e.g., from 1:10 to 10:1 or from 1:3 to 3:1. In one aspect, not shown, the second distillate 161 or a portion thereof may be returned to the reaction zone (shown in FIGS. 1A-1C). The ethyl acetate and/or acetaldehyde in the second distillate may be further reacted in reaction zone.

In one embodiment, the second distillate in line 161 and/or a refined second distillate, or a portion of either or both streams, may be further separated to produce an acetaldehyde-containing stream and an ethyl acetate-containing stream similar to the optional fourth column in FIG. 1C. This may allow a portion of either the resulting acetaldehyde-containing stream or ethyl acetate-containing stream to be recycled to the reactor while purging the other stream. The purge stream may be valuable as a source of either ethyl acetate and/or acetaldehyde.

FIG. 3 is another exemplary separation system to recover a mixed alcohol stream comprising ethanol and the heavier alcohol from the second reaction mixture. Stream 115 is introduced in the upper part of first column 170, e.g., upper half or upper third. In one embodiment, no entrainers are added to first column 170. In first column 170, a weight majority of the ethanol, higher alcohol, water, acetic acid, higher acid, and other heavy components, if present, are removed from stream 115 and are withdrawn, preferably continuously, as residue in line 171. First column 170 also forms an overhead distillate, which is withdrawn in line 172, and which may be condensed and refluxed, for example, at a ratio of from 30:1 to 1:30, e.g., from 10:1 to 1:10 or from 1:5 to 5:1. The overhead distillate in stream 172 preferably comprises a weight majority of the ethyl acetate from stream 115.

When column 170 is operated under about 170 kPa, the temperature of the residue exiting in line 171 preferably is from 70° C. to 155° C., e.g., from 90° C. to 130° C. or from 100° C. to 110° C. The base of column 170 may be maintained at a relatively low temperature by withdrawing a residue stream comprising ethanol, higher alcohol(s), water, acetic acid, and higher acid(s), thereby providing an energy efficiency advantage. The temperature of the distillate exiting in line 172 preferably at 170 kPa is from 75° C. to 100° C., e.g., from 75° C. to 83° C. or from 81° C. to 84° C. In some embodiments, the pressure of first column 170 may range from 0.1 kPa to 510 kPa, e.g., from 1 kPa to 475 kPa or from 1 kPa to 375 kPa. Exemplary components of the distillate and residue compositions for first column 170 are provided in Table 9 below. It should also be understood that the distillate and residue may also contain other components, not listed in Table 9.

TABLE 9

FIRST COLUMN 170 (FIG. 3)

|  | Conc. (wt. %) | Conc. (wt. %) | Conc. (wt. %) |
|---|---|---|---|
| Distillate | | | |
| Ethyl Acetate | 10 to 85 | 15 to 80 | 20 to 75 |
| Acetaldehyde | <0.1 | 0.0001 to 0.05 | 0.005 to 0.025 |
| Acetal | <0.1 | 0.0001 to 0.05 | 0.005 to 0.025 |
| Acetone | <0.05 | 0.001 to 0.03 | 0.01 to 0.025 |
| Ethanol | 3 to 55 | 4 to 50 | 5 to 45 |
| Higher Alcohol* | 3 to 55 | 4 to 50 | 5 to 45 |
| Water | 0.1 to 20 | 1 to 15 | 2 to 10 |
| Acetic Acid | <2 | <0.1 | <0.05 |
| Higher Acid** | <2 | <0.1 | <0.05 |
| Residue | | | |
| Acetic Acid | 0.01 to 35 | 0.1 to 30 | 0.2 to 25 |
| Higher Acid** | 0.01 to 35 | 0.1 to 30 | 0.2 to 25 |
| Water | 25 to 70 | 30 to 65 | 35 to 60 |
| Ethanol | 10 to 75 | 15 to 70 | 20 to 65 |
| Higher Alcohol* | 0.01 to 20 | 0.04 to 20 | 0.5 to 10 |

In an embodiment of the present invention, column 170 may be operated at a temperature where most of the water, ethanol, higher alcohol, acetic acid, and higher acid are removed from the residue stream and only a small amount of ethanol, higher alcohol, and water is collected in the distillate stream due to the formation of binary and tertiary azeotropes. The weight ratio of water in the residue in line 171 to water in the distillate in line 172 may be greater than 1:1, e.g., greater than 2:1. The weight ratio of alcohols in the residue to alcohols in the distillate may be greater than 1:1, e.g., greater than 2:1

The amount of acids in the first residue may vary depending primarily on the conversion in the reaction zone. In one embodiment, when the conversion is high, e.g., greater than 90%, the amount of acid (collectively) in the first residue may be less than 10 wt. %, e.g., less than 5 wt. % or less than 2 wt. %. In other embodiments, when the conversion is lower, e.g., less than 90%, the amount of acid in the first residue may be greater than 10 wt. %.

The distillate preferably is substantially free of acid, e.g., comprising less than 1000 ppm, less than 500 ppm or less than 100 ppm acetic acid and higher acid. The distillate may be purged from the system or recycled in whole or part to reaction zone. In some embodiments, the distillate may be further separated, e.g., in a distillation column (not shown), into an acetaldehyde stream and an ethyl acetate stream. Either of these streams may be returned to the reaction zone or separated from the system as a separate product.

Some species, such as acetals, may decompose in first column 170 such that very low amounts, or even no detectable amounts, of acetals remain in the distillate or residue.

To recover the ethanol and higher alcohols, the residue in line 171 may be further separated in a second column 173, also referred to as an "acid separation column." An acid separation column may be used when the acid concentration (acetic acid and higher acid concentration) in the first residue is greater than 1 wt. %, e.g., greater than 5 wt. %. The first residue in line 171 is introduced to second column 173 preferably in the top part of column 173, e.g., top half or top third. Second column 173 yields a second residue in line 174 comprising acetic acid, higher acid and water, and a second distillate in line 175 comprising ethanol and the higher alcohol. Second column 173 may be a tray column or packed column. In one embodiment, second column 173 is a tray column having from 5 to 150 trays, e.g., from 15 to 50 trays or from 20 to 45 trays. Although the temperature and pressure of second column 173 may vary, when at atmospheric pressure the temperature of the second residue exiting in line 174 preferably is from 95° C. to 130° C., e.g., from 100° C. to 125° C. or from 110° C. to 120° C. The temperature of the second distillate exiting in line 175 preferably is from 60° C. to 105° C., e.g., from 75° C. to 100° C. or from 80° C. to 100° C. The pressure of second column 173 may range from 0.1 kPa to 510 kPa, e.g., from 1 kPa to 475 kPa or from 1 kPa to 375 kPa. Exemplary components for the distillate and residue compositions for second column 173 are provided in Table 10 below. It should be understood that the distillate and residue may also contain other components, not listed in Table 10.

TABLE 10

| SECOND COLUMN 173 (FIG. 3) | | | |
|---|---|---|---|
| | Conc. (wt. %) | Conc. (wt. %) | Conc. (wt. %) |
| Second Distillate | | | |
| Ethanol | 70 to 99.9 | 75 to 99.5 | 80 to 99.5 |
| Higher Alcohol* | 0.01 to 20 | 0.01 to 20 | 0.5 to 10 |
| Ethyl Acetate | <10 | 0.001 to 5 | 0.01 to 3 |

TABLE 10-continued

| SECOND COLUMN 173 (FIG. 3) | | | |
|---|---|---|---|
| | Conc. (wt. %) | Conc. (wt. %) | Conc. (wt. %) |
| Acetaldehyde | <5 | 0.001 to 1 | 0.005 to 0.5 |
| Water | 0.1 to 30 | 0.5 to 25 | 0.5 to 20 |
| Second Residue | | | |
| Acetic Acid | 0.1 to 45 | 0.2 to 40 | 0.5 to 35 |
| Higher Acid** | 0.01 to 30 | 0.2 to 20 | 0.5 to 10 |
| Water | 45 to 100 | 55 to 99.8 | 65 to 99.5 |
| Ethyl Acetate | <2 | <1 | <0.5 |
| Ethanol | <5 | 0.001 to 5 | <2 |
| Higher Alchol* | <5 | 0.001 to 5 | <2 |

The weight ratio of alcohols in the second distillate in line 175 to alcohols in the second residue in line 174 preferably is at least 35:1. In one embodiment, the weight ratio of water in the second residue 174 to water in the second distillate 175 is greater than 2:1, e.g., greater than 4:1 or greater than 6:1. In addition, the weight ratio of acids in the second residue 174 to acids in the second distillate 175 preferably is greater than 10:1, e.g., greater than 15:1 or greater than 20:1. Preferably, the second distillate in line 175 is substantially free of acetic acid and higher acid and may only contain, if any, trace amounts of acid. Preferably, the second distillate in line 175 contains substantially no ethyl acetate.

The remaining water from the second distillate in line 175 may be removed in further embodiments of the present invention. Depending on the water concentration, the alcohol product, comprising ethanol and higher alcohol, may be derived from the second distillate in line 175. Some ethanol applications, such as industrial ethanol applications, may tolerate water in the product, while other applications, such as fuel applications, may require an anhydrous composition. The amount of water in the distillate of line 175 may be closer to the azeotropic amount of water, e.g., at least 4 wt. %, preferably less than 20 wt. %, e.g., less than 12 wt. % or less than 7.5 wt. %. Water may be removed from the second distillate in line 175 using several different separation techniques as described herein. Particularly preferred techniques include the use of distillation column, membranes, adsorption units, and combinations thereof.

Some of the residues withdrawn from the separation systems shown in FIGS. 1-3, may comprise acetic acid, higher acid, and water. Depending on the amount of water, acetic acid and higher acid contained in the residue of first column, e.g., 150 in FIG. 2, or residue of second column 173 in FIG. 3, the residue may be treated in one or more of the following processes. The following are exemplary processes for further treating the residue and it should be understood that any of the following may be used regardless of acid concentration. When the residue comprises a majority of acetic acid and heavier acid, e.g., greater than 70 wt. %, the residue may be recycled to the reactor without any separation of the water. In one embodiment, the residue may be separated into an acid stream and a water stream when the residue comprises a majority of acetic acid and heavier acid, e.g., greater than 50 wt. %. Acid may also be recovered in some embodiments from the residue having a lower acid concentration. The residue may be separated into the acid and water streams by a distillation column or one or more membranes. If a membrane or an array of membranes is employed to separate the acid from the water, the membrane or array of membranes may be selected from any suitable acid resistant membrane that is capable of removing a permeate water stream. The resulting acid stream comprising acetic acid and heavier acid optionally is returned to the first reaction zone 102. The resulting water stream may be used as an extractive agent or to hydrolyze an ester-containing stream in a hydrolysis unit.

In other embodiments, for example, where the residue comprises less than 50 wt. % acid, possible options include one or more of: (i) returning a portion of the residue to reactor 103, (ii) neutralizing the acid, (iii) reacting the acid with an alcohol, or (iv) disposing of the residue in a waste water treatment facility. It also may be possible to separate a residue comprising less than 50 wt. % acid using a weak acid recovery distillation column to which a solvent (optionally acting as an azeotroping agent) may be added. Exemplary solvents that may be suitable for this purpose include ethyl acetate, propyl acetate, isopropyl acetate, butyl acetate, vinyl acetate, diisopropyl ether, carbon disulfide, tetrahydrofuran, isopropanol, ethanol, and $C_3$-$C_{12}$ alkanes. When neutralizing the acid, it is preferred that the residue comprises less than 10 wt. % acid (acetic acid and higher acid in combination). The acid may be neutralized with any suitable alkali or alkaline earth metal base, such as sodium hydroxide or potassium hydroxide. When reacting acid with an alcohol, it is preferred that the residue comprises less than 50 wt. % acid. The alcohol may be any suitable alcohol, such as methanol, ethanol, propanol, butanol, or mixtures thereof. The reaction forms an ester that may be integrated with other systems, such as carbonylation production or an ester production process. Preferably, the alcohol comprises ethanol and the resulting ester comprises ethyl acetate. Optionally, the resulting ester may be fed to the hydrogenation reactor.

In some embodiments, when the residue comprises very minor amounts of acid, e.g., less than 5 wt. %, the residue may be disposed of to a waste water treatment facility without further processing. The organic content, e.g., acid content, of the residue beneficially may be suitable to feed microorganisms used in a waste water treatment facility.

The columns shown in figures may comprise any distillation column capable of performing the desired separation and/or purification. Each column preferably comprises a tray column having from 1 to 150 trays, e.g., from 10 to 100 trays, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in two or more columns such that the vapor from the first section enters the second section while the liquid from the second section enters the first section, etc.

The associated condensers and liquid separation vessels that may be employed with each of the distillation columns may be of any conventional design and are simplified in the figures. Heat may be supplied to the base of each column or to a circulating bottom stream through a heat exchanger or reboiler. Other types of reboilers, such as internal reboilers, may also be used. The heat that is provided to the reboilers may be derived from any heat generated during the process that is integrated with the reboilers or from an external source such as another heat generating chemical process or a boiler. Although one reactor and one flasher are shown in the figures, additional reactors, flashers, condensers, heating elements, and other components may be used in various embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in the columns may vary. As a practical matter, pressures from 10 kPa to 3000 kPa will generally be employed in these zones although in some embodiments subatmospheric pressures or superatmospheric pressures may be employed. Temperatures within the various zones will normally range between the boiling points of the composition removed as the distillate and the composition removed as the residue. As will be recognized by those skilled in the art, the temperature at a given location in an operating distillation column is dependent on the composition of the material at that location and the pressure of column. In addition, feed rates may vary depending on the size of the production process and, if described, may be generically referred to in terms of feed weight ratios.

The final alcohol product produced by the processes of the present invention may be taken from a stream that primarily comprises ethanol and/or heavier alcohols from FIGS. 1-3. The alcohol product may be an industrial grade ethanol composition comprising from 75 to 96 wt. % ethanol, e.g., from 80 to 96 wt. % or from 85 to 96 wt. % ethanol, based on the total weight of the ethanol product. Depending on the embodiment of the invention, the finished alcohol product may include a minor or a substantial amount of heavier alcohols, or may be substantially free of any heavier alcohols if, for example, the heavier alcohols are separated from the ethanol during processing. Non-limiting exemplary finished alcohol compositional ranges are provided below in Table 11.

TABLE 11

FINISHED ALCOHOL COMPOSITIONS

| Component | Conc. (wt. %) | Conc. (wt. %) | Conc. (wt. %) | Conc. (wt. %) | Conc. (wt. %) |
|---|---|---|---|---|---|
| Ethanol | 75 to 99.9 | 80 to 99.5 | 85 to 96 | 85 to 96 | 85 to 96 |
| Heavier Alcohol* | 0.01 to 20 | 0.04 to 20 | 0.5 to 10 | 1 to 8 | 2 to 5 |
| Water | <12 | 1 to 9 | 3 to 8 | 3 to 8 | 3 to 8 |
| Acetic Acid | <1 | <0.1 | <0.01 | <0.01 | <0.01 |
| Heavier Acid** | <1 | <0.1 | <0.01 | <0.01 | <0.01 |
| Ethyl Acetate | <2 | <0.5 | <0.05 | <0.05 | <0.05 |
| Acetal | <0.05 | <0.01 | <0.005 | <0.005 | <0.005 |
| Acetone | <0.05 | <0.01 | <0.005 | <0.005 | <0.005 |

As discussed above, although in some embodiments the finished alcohol composition may comprise a substantial amount of higher alcohols, in some embodiments, the finished ethanol composition of the present invention contains very low amounts, e.g., less than 0.5 wt. %, of other alcohols, such as methanol, butanol, n-propanol, isobutanol, isoamyl alcohol and other higher alcohols. In one embodiment, the amount of isopropanol in the finished alcohol composition is from 80 to 1,000 wppm, e.g., from 95 to 1,000 wppm, from 100 to 700 wppm, or from 150 to 500 wppm. In one embodiment, the finished alcohol composition is substantially free of acetaldehyde, optionally comprising less than 8 wppm acetaldehyde, e.g., less than 5 wppm or less than 1 wppm.

In one aspect, the process forms separate ethanol and higher alcohol streams. For example, the separating step optionally comprises the steps of separating the crude alcohol product into an ethanol stream and a higher alcohol stream; purifying the ethanol stream to form a purified ethanol stream; and purifying the higher alcohol stream to form a purified higher alcohol stream. In this aspect, the above-discussed finished alcohol composition comprising a low amount of higher alcohols may comprise the purified ethanol stream. Conversely, the purified higher alcohol stream may comprise the higher alcohol in an amount greater than 60 wt. %, greater than 75 wt. % or greater than 90 wt. %, and may comprise ethanol in a relatively small amount, e.g., an amount less than 40 wt. %, less than 25 wt. %, or less than 10 wt. %. If desired, the resulting ethanol and/or propanol compositions may be dehydrated, optionally in the presence of a catalyst, to form ethylene and/or propylene, respectively. See, e.g., U.S. Pat. No. 7,199,276 and US Publ. No. 2009/0259086, the entireties of which are incorporated herein by reference.

In some embodiments, when further water separation is used, the alcohol product may be withdrawn as a stream from the water separation unit as discussed above. In such embodiments, the ethanol concentration of the alcohol product may be greater than indicated in Table 11, and may be greater than 97 wt. % ethanol, e.g., greater than 98 wt. % or greater than 99.5 wt. %. The alcohol product in this aspect preferably comprises less than 3 wt. % water, e.g., less than 2 wt. % or less than 0.5 wt. %.

Denatured Ethanol Compositions

As noted above, the alcohol composition formed by the processes of the invention may constitute a denatured ethanol composition comprising ethanol and at least one, e.g., at least two or at least three, denaturants. The denaturant may be produced in situ via the hydrogenation reaction, thus eliminating the need for an outside denaturant source. Preferably, the denaturant comprises one or more heavier alcohols, preferably comprising propanol, formed from the hydrogenation of one or more heavier acids, preferably comprising propionic acid. Additionally, the denaturant may comprise one or more of ethyl acetate, acetaldehyde, diethyl ether, acetic acid, isopropanol and/or mixtures thereof.

The denaturant, thus produced, should be present in an effective amount, e.g., in an amount sufficient to provide for a denatured ethanol composition in accordance with appropriate government regulations. As used herein, the term "denatured ethanol composition" means a composition comprising ethanol and one or more denaturants that is unfit for beverage or internal human medicine, e.g., unpalatable. In other embodiments, the denatured ethanol may comprise a "specifically denatured ethanol," which is an ethanol composition that is denatured pursuant to the formulae authorized under 27 C.F.R. Part 21, Subpart D. In addition, requirements for denatured ethanols are different for different applications, e.g., fuel applications and industrial applications. Thus, some applications may require higher amounts of denaturants while other applications may require lower amounts. Fuel uses for ethanol may necessitate supplementing the denatured mixed alcohol composition of the invention with one or more fuel denaturants that are suitable for fuel uses. Such fuel denaturants may vary depending on country and region, but some examples include natural gasoline, gasoline blendstocks or unleaded gasoline. A listing of some of these applications is provided in 27 C.F.R. Part 21, the entirety of which is incorporated herein by reference. Table 12 indicates some of the denatured compositions in terms of the amount of denaturant that is added to 100 gallons of ethanol.

TABLE 12

US Denatured Alcohol Formulae According to 27 C.F.R. Part 21

| Formula | Denaturant | Amount (gallons) |
|---|---|---|
| Formula 3-C | isopropyl alcohol | 5 |
| Formula 13-A | ethyl ether | 10 |
| Formula 18* | vinegar 90-grain strength (9% acetic acid in water) | 100 |

TABLE 12-continued

US Denatured Alcohol Formulae According to 27 C.F.R. Part 21

| Formula | Denaturant | Amount (gallons) |
|---|---|---|
| Formula 18* | vinegar 60-grain strength (6% acetic acid in water) | 150 |
| Formula 29 | acetaldehyde | 1 |
| Formula 29 | alcohol solution containing not less than 20% acetaldehyde | 5 |
| Formula 29 | ethyl acetate | 1 |
| Formula 32 | ethyl ether | 5 |
| Formula 35 | ethyl acetate | 29.75 |
| Formula 35 | mixture of ethyl acetate with an ester content of not less than 85 percent by weight | 35 |
| Formula 35-A | ethyl acetate | 4.25 |
| Formula 35-A | mixture of ethyl acetate with an ester content of not less than 85 percent by weight | 5 |

*Ethanol is not less than 160 proof.

In addition, in other embodiments, the inventive denatured ethanol compositions, as formed, correspond to the denatured formulae of countries other than the United States. For example, in the United Kingdom, one formula for trade specific denatured alcohol is as follows. With every 979 parts by volume of alcohol (of a strength of not less than 85 percent alcohol by volume) mix not less than 20 parts by volume of ethyl acetate and 1 part by volume of isopropyl alcohol.

Another exemplary United Kingdom trade specific denatured alcohol formula is as follows. With every 950 parts by volume of alcohol (of a strength of not less than 85 percent alcohol by volume) mix not less than 50 parts by volume of isopropyl alcohol.

Of course, this listing of US and international denatured ethanol composition formulae is not exclusive and other formula are within the scope of the invention.

Preferably, the denatured ethanol composition comprises from 50 wt. % to 99 wt. % ethanol, e.g., from 60 wt. % to 99 wt. % or from 70 wt. % to 95 wt. %, and from 0.01 wt. % to 40 wt. % denaturant, e.g., from 0.01 wt. % to 25 wt. %, from 0.01 wt. % to 20 wt. %, or from 1 wt. % to 15 wt. %, based on the total weight of the denatured ethanol composition.

In some embodiments, the inventive denatured ethanol composition comprises at least a portion of the first column distillate of FIG. 1A-C, as discussed above. Here, the denatured ethanol composition may comprise as the denaturant ethyl acetate and/or acetaldehyde. Preferably, the amount of total denaturant (ethyl acetate and acetaldehyde) in these denatured ethanol compositions ranges from 0.01 wt. % to 90 wt. % denaturant, e.g., from 0.01 wt. % to 65 wt. % or from 0.01 wt. % to 34 wt. %.

In some embodiments, the ethanol composition comprises an ethyl ether, e.g., diethyl ether, denaturant in an amount ranging from 0.1 wt. % to 20 wt. % diethyl ether, e.g., from 0.1 wt. % to 10 wt. %, from 1 wt. % to 9 wt. % or from 3 wt. % to 7 wt. %. In other embodiments, the ethanol composition comprises an acetic acid denaturant in an amount ranging from 0.1 wt. % to 20 wt. % acetic acid, e.g., from 1 wt. % to 15 wt. % or from 2 wt. % to 12 wt. %. In other embodiments, the ethanol composition comprises a heavier alcohol denaturant, such as n-propanol, in an amount ranging from 0.001 wt. % to 10 wt. % n-propanol, e.g., from 0.001 wt. % to 0.1 wt. %, from 0.1 wt. % to 10 wt. %, from 1 wt. % to 9 wt. %, or from 3 wt. % to 7 wt. %.

In preferred embodiments, the denatured ethanol composition is formed by combining a crude alcohol product derivative stream comprising denaturant, e.g., the second distillate, and a purified mixed alcohol stream, which comprises ethanol and one or more heavier alcohols. Exemplary weight percentage ranges for the ethanol, heavier alcohol(s) and the denaturants, e.g., ethyl acetate and/or acetaldehyde, (as well as other optional components) are provided in Table 13. In some embodiments, the ethanol composition comprises an ethyl acetate denaturant in an amount ranging from 0.01 wt. % to 40 wt. % ethyl acetate, e.g., from 0.01 wt. % to 15 wt. %, from 0.01 wt. % to 10 wt. % or from 0.01 wt. % to 9 wt. %. In other embodiments, the denatured ethanol composition comprises an acetaldehyde denaturant in an amount ranging from 0.01 wt. % to 10 wt. % acetaldehyde, e.g., from 0.01 wt. % to 5 wt. %, from 0.01 wt. % to 2 wt. % or from 0.01 wt. % to 1 wt. %. Preferably, the amount of total denaturant in these denatured ethanol compositions ranges from 0.01 wt. % to 20 wt. % denaturant, e.g., from 0.01 wt. % to 12 wt. % or from 0.01 wt. % to 10 wt. %.

TABLE 13

DENATURED ETHANOL COMPOSITIONS

| Component | Conc. (wt. %) | Conc. (wt. %) | Conc. (wt. %) |
|---|---|---|---|
| Ethanol | 50 to 99 | 60 to 99 | 70 to 95 |
| Water | 0.0001 to 1 | 0.001 to 0.1 | 0.001 to 0.05 |
| Acetic Acid | 1 to 20 | 3 to 15 | 5 to 10.5 |
| Higher Acid** | <10 | 0.01 to 5 | 0.1 to 2 |
| Heavier Alcohol* (Denaturant) | 0.01 to 20 | 0.04 to 20 | 0.5 to 10 |
| Ethyl Acetate (Denaturant) | <15 | <10 | <9 |
| Acetaldehyde (Denaturant) | <10 | <5 | <3 |
| Isopropanol (Denaturant) | 0.05 to 10 | 0.6 to 9 | 2 to 6.7 |
| Diethyl Ether (Denaturant) | 0.05 to 10 | 0.6 to 9 | 2 to 6.7 |
| N-propanol (Denaturant) | 0.05 to 10 | 0.6 to 9 | 2 to 6.7 |
| Acetal | <0.05 | <0.01 | <0.005 |
| Acetone | <0.05 | <0.01 | <0.005 |

Although the exemplary weight percentages of water in the embodiments of Table 13 range from 0.0001 wt. % to 1 wt. %, in other embodiments, water may be present in the denatured ethanol composition in greater amounts. For example, the denatured ethanol composition may comprise water in an amount ranging from 0.1 wt. % to 8 wt. % water, e.g., from 0.1 wt. % to 5 wt. % or from 0.1 wt. % to 2 wt. %.

The denatured ethanol compositions of the embodiments of the present invention may be suitable for use in a variety of applications including fuels, solvents, chemical feedstocks, pharmaceutical products, cleansers, sanitizers, or hydrogenation transport. In fuel applications, the denatured ethanol composition may be blended with gasoline for motor vehicles such as automobiles, boats and small piston engine aircrafts. In non-fuel applications, the denatured ethanol composition may be used as a solvent for toiletry and cosmetic preparations, detergents, disinfectants, coatings, inks, and pharmaceuticals. The denatured ethanol composition may also be used as a processing solvent, e.g., in manufacturing processes for medicinal products, food preparations, dyes, photochemicals and latex processing.

The denatured ethanol composition may also be used as a chemical feedstock to make other chemicals such as vinegar, ethyl acrylate, ethyl acetate, ethylene, glycol ethers, ethylamines, aldehydes, and higher alcohols, especially butanol. The higher alcohol, preferably propanol, separately or in combination with ethanol, similarly may be used as a chemical feedstock to make propyl acetate, propylene, propylamines, aldehydes or $C_{4+}$ alcohols. The denatured ethanol composition may be suitable for use as a feed stock in esters production. Preferably, in the production of ethyl acetate, the denatured ethanol composition may be esterified with acetic acid or reacted with polyvinyl acetate. The denatured ethanol composition may be dehydrated to produce ethylene. Any of known dehydration catalysts can be employed to dehydrate ethanol, such as those described in copending U.S. application Ser. No. 12/221,137 and U.S. application Ser. No. 12/221,138, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated by reference.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing an alcohol composition, the process comprising:
   (a) carbonylating methanol in a carbonylation reactor to form a mixed acid feed comprising acetic acid and at least 0.01 wt. % heavier acid;
   (b) hydrogenating the mixed acid feed comprising acetic acid in the presence of a catalyst to form a crude alcohol product comprising ethanol and a higher alcohol; and
   (c) separating the crude alcohol product in one or more separation units to form an alcohol composition and one or more derivative streams.

2. The process of claim 1, wherein the carbonylating forms a crude acetic acid product, the process further comprising the steps of:
   separating the crude acetic acid product in a flash unit to form a flashed stream and a catalyst recycle stream; and
   separating, in no more than one separation column, the flashed stream into a distillate comprising an alkyl halide and an alkyl acetate, and a residue comprising the mixed acid feed.

3. The process of claim 1, wherein the mixed acid feed comprises from 0.04 to 20 wt. % propionic acid.

4. The process of claim 1, wherein the mixed acid feed comprises from 0.5 to 10 wt. % propionic acid.

5. The process of claim 1, wherein the mixed acid feed comprises from 1 to 8 wt. % propionic acid.

6. The process of claim 1, wherein the mixed acid feed comprises the acetic acid in an amount from 80 to 99 wt. % and the higher acid in an amount from 0.01 to 20 wt. %.

7. The process of claim 1, wherein the alcohol composition comprises less than 1 wt. % higher alcohols.

8. The process of claim 1, wherein the alcohol composition comprises from 0.01 to 20 wt. % higher alcohols.

9. The process of claim 1, wherein the alcohol composition comprises from 0.04 to 20 wt. % higher alcohols.

10. The process of claim 1, wherein the alcohol composition comprises from 0.5 to 10 wt. % higher alcohols.

11. The process of claim 1, wherein the alcohol composition comprises less than 0.5 wt. % higher alcohols.

12. The process of claim 1, wherein the higher acid is propionic acid.

13. The process of claim 1, wherein the higher acid is propionic acid, and the mixed acid feed comprises at least 0.04 wt. % propionic acid.

14. The process of claim 1, wherein the higher acid is propionic acid, and the mixed acid feed comprises at least 0.08 wt. % propionic acid.

15. The process of claim 1, wherein the higher acid is propionic acid, and the mixed acid feed comprises at least 0.5 wt % propionic acid.

16. The process of claim 1, wherein the alcohol composition comprises from 92 wt. % to 99 wt. % ethanol.

17. The process of claim 1, wherein the alcohol composition comprises from 92 to 99 wt. % ethanol and from 0.01 to 8 wt % propanol.

18. The process of claim 1, wherein the catalyst comprises iridium.

19. The process of claim 1, wherein the catalyst comprises rhodium.

20. The process of claim 1, wherein the mixed acid feed comprises acetic acid, the higher acid and acetone, and the crude alcohol product further comprises isopropanol.

21. The process of claim 1, wherein the separating comprises:
   separating a first portion of the crude alcohol product into an ethanol stream and a higher alcohol stream;
   purifying the ethanol stream to form a purified ethanol stream; and
   combining at least a portion of the higher alcohol stream with the purified ethanol stream to form the alcohol composition.

22. A process for producing a mixed alcohol composition, the process comprising:
   (a) carbonylating methanol in a carbonylation reactor to form a mixed acid feed comprising acetic acid and a heavier acid;
   (b) hydrogenating the mixed acid feed comprising acetic acid in the presence of a catalyst to form a crude alcohol product comprising ethanol and a higher alcohol; and
   (c) separating the crude alcohol product in one or more separation units to form a mixed alcohol composition and one or more derivative streams, wherein the mixed alcohol composition comprises ethanol in an amount greater than 60 wt. % and the higher alcohol in an amount from 0.01 wt. % to 40 wt %, based on the total weight of the mixed alcohol composition.

23. The process of claim 22, wherein the carbonylating forms a crude acetic acid product, the process further comprising the steps of:
   separating the crude acetic acid product in a flash unit to form a flashed stream and a catalyst recycle stream; and
   separating, in no more than one separation column, the flashed stream into a distillate comprising an alkyl halide and an alkyl acetate, and a residue comprising the mixed acid feed.

24. The process of claim 22, wherein the mixed acid feed comprises from 0.04 to 20 wt. % propionic acid.

25. The process of claim 22, wherein the mixed acid feed comprises from 0.5 to 10 wt. % propionic acid.

26. The process of claim 22, wherein the mixed acid feed comprises from 1 to 8 wt. % propionic acid.

27. The process of claim 22, wherein the mixed acid feed comprises the acetic acid in an amount from 80 to 99 wt. % and the higher acid in an amount from 0.01 to 20 wt. %.

28. The process of claim 22, wherein the alcohol composition comprises less than 1 wt. % higher alcohols.

29. The process of claim 22, wherein the alcohol composition comprises from 0.01 to 20 wt. % higher alcohols.

30. The process of claim 22, wherein the alcohol composition comprises from 0.04 to 20 wt. % higher alcohols.

31. The process of claim 22, wherein the alcohol composition comprises from 0.5 to 10 wt. % higher alcohols.

32. The process of claim 22, wherein the alcohol composition comprises less than 0.5 wt. % higher alcohols.

33. The process of claim 22, wherein the higher acid is propionic acid.

34. The process of claim 22, wherein the higher acid is propionic acid, and the mixed acid feed comprises at least 0.04 wt. % propionic acid.

35. The process of claim 22, wherein the higher acid is propionic acid, and the mixed acid feed comprises at least 0.08 wt. % propionic acid.

36. The process of claim 22, wherein the higher acid is propionic acid, and the mixed acid feed comprises at least 0.5 wt % propionic acid.

37. The process of claim 22, wherein the alcohol composition comprises from 92 wt. % to 99 wt. % ethanol.

38. The process of claim 22, wherein the alcohol composition comprises from 92 to 99 wt. % ethanol and from 0.01 to 8 wt % propanol.

39. The process of claim 22, wherein the catalyst comprises iridium.

40. The process of claim 22, wherein the catalyst comprises rhodium.

41. The process of claim 22, wherein the mixed acid feed comprises acetic acid, the higher acid and acetone, and the crude alcohol product further comprises isopropanol.

42. The process of claim 22, wherein the separating comprises:
   separating a first portion of the crude alcohol product into an ethanol stream and a higher alcohol stream;
   purifying the ethanol stream to form a purified ethanol stream; and
   combining at least a portion of the higher alcohol stream with the purified ethanol stream to form the alcohol composition.

* * * * *